US012685490B2

(12) United States Patent
Armiento et al.

(10) Patent No.: US 12,685,490 B2
(45) Date of Patent: Jul. 21, 2026

(54) METHOD OF PREVENTING OR TREATING PANCREATIC DYSFUNCTION OR DIABETES BY UPREGULATING HUMAN CATHELICIDIN LL-37 TO INHIBIT ISLET AMYLOID POLYPEPTIDE (IAPP) SELF-ASSEMBLY

(71) Applicant: The Board of Trustees of the Leland Stanford Junior University, Stanford, CA (US)

(72) Inventors: Valentina Armiento, Kranzberg (DE); Annelise E. Barron, Woodside, CA (US); Aphrodite Kapurniotu, Muenich (DE); John A. Fortkort, Austin, TX (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 924 days.

(21) Appl. No.: 17/759,710

(22) PCT Filed: Jan. 28, 2021

(86) PCT No.: PCT/US2021/015531

§ 371 (c)(1),
(2) Date: Jul. 28, 2022

(87) PCT Pub. No.: WO2021/155025

PCT Pub. Date: Aug. 5, 2021

(65) Prior Publication Data

US 2024/0268768 A1 Aug. 15, 2024

Related U.S. Application Data

(60) Provisional application No. 62/967,023, filed on Jan. 28, 2020.

(51) Int. Cl.

| | |
|---|---|
| ***A61K 31/164*** | (2006.01) |
| ***A61B 5/00*** | (2006.01) |
| ***A61B 5/145*** | (2006.01) |
| ***G06T 7/00*** | (2017.01) |

(52) U.S. Cl.

CPC ........ *A61B 5/7275* (2013.01); *A61B 5/14532* (2013.01); *A61B 5/14546* (2013.01); *A61K 31/164* (2013.01); *G06T 7/0012* (2013.01)

(58) Field of Classification Search

None

See application file for complete search history.

(56) References Cited

U.S. PATENT DOCUMENTS

| | | | |
|---|---|---|---|
| 7,658,928 B2 | 2/2010 | Fritz et al. | |
| 7,829,556 B2 | 11/2010 | Bemis et al. | |
| 8,445,632 B2 | 5/2013 | Barron et al. | |
| 8,673,842 B2 | 3/2014 | Barron et al. | |
| 8,828,413 B2 | 9/2014 | Kirshenbaum et al. | |
| 9,078,864 B2 | 7/2015 | Gudmundsson et al. | |
| 9,315,548 B2 | 4/2016 | Kirshenbaum et al. | |
| 9,938,321 B2 | 4/2018 | Kirshenbaum et al. | |
| 9,957,226 B2 | 5/2018 | Stromberg et al. | |
| 2006/0115480 A1 | 6/2006 | Hillman | |
| 2007/0032421 A1 | 2/2007 | Levy | |
| 2007/0299041 A1 | 12/2007 | Gombart et al. | |
| 2008/0038374 A1 | 2/2008 | Stahle et al. | |
| 2008/0081781 A1 | 4/2008 | Lippa et al. | |
| 2008/0166368 A1 | 7/2008 | Fritz et al. | |
| 2009/0048167 A1 | 2/2009 | Hillman | |
| 2009/0060843 A1 | 3/2009 | Berggren et al. | |
| 2009/0088394 A1 | 4/2009 | Robbins | |
| 2009/0093434 A1 | 4/2009 | Thompson et al. | |
| 2010/0087406 A1* | 4/2010 | Gombart .............. | A61K 31/593 514/168 |
| 2010/0087527 A1 | 4/2010 | Dimauro | |
| 2010/0210539 A1 | 8/2010 | Bevec et al. | |
| 2010/0297150 A1 | 11/2010 | Hillman | |
| 2011/0059483 A1 | 3/2011 | Inagaki et al. | |
| 2011/0118217 A1 | 5/2011 | Gudmundsson et al. | |
| 2011/0243992 A1 | 10/2011 | Kernodle | |
| 2012/0058935 A1 | 3/2012 | Moir et al. | |
| 2013/0123201 A1 | 5/2013 | Mookherjee | |

(Continued)

FOREIGN PATENT DOCUMENTS

| | | |
|---|---|---|
| CA | 2508273 A1 | 7/2004 |
| CN | 115361961 A | 11/2022 |

(Continued)

OTHER PUBLICATIONS

Pesce et al., "PD/1-PD-Ls Checkpoint: Insight on the Potential Role of NK Cells", Frontiers in Immunology, vol. 10, Article 1242, Jun. 4, 2019, 8 pgs., doi: 10.3389/fimmu.2019.01242.
Pfosser et al., "Nf Kb Activation in Embryonic Endothelial Progenitor Cells Enhances Neovascularization Via PSGL-1 Mediated Recruitment: Novel Role for LL37", Stem Cells, vol. 28, No. 2, Feb. 2010, pp. 376-385, doi: 10.1002/stem.280.
Pinegin et al., "Neutrophil extracellular traps and their role in the development of chronic inflammation and autoimmunity", Autoimmunity Reviews, vol. 14, No. 7, Jul. 2015, pp. 633-640, doi: 10.1016/j.autrev.2015.03.002.
Pinkenburg et al., "Recombinant Adeno-Associated Virus-Based Gene Transfer of Cathelicidin Induces Therapeutic Neovascularization Preferentially via Potent Collateral Growth", Human Gene Therapy, vol. 20, No. 2, Feb. 2009, pp. 159-167, doi: 10.1089/hum.2007.178.

(Continued)

*Primary Examiner* — Samantha L Shterengarts
(74) *Attorney, Agent, or Firm* — KPPB LLP

(57) ABSTRACT

A method for treating type 2 diabetes (T2D) is provided. The method comprises diagnosing a subject as suffering from T2D or as being pre-diabetic; monitoring the response to glucose stimulation of at least one islet in the pancreas of the subject by quantitatively imaging glucose metabolism in vivo; establishing a target range for the response to glucose stimulation of the at least one islet; and upregulating cathelicidin gene expression in the subject until the monitored response to glucose stimulation is within the target range.

20 Claims, 25 Drawing Sheets

Specification includes a Sequence Listing.

(56) References Cited

U.S. PATENT DOCUMENTS

| | | | |
|---|---|---|---|
| 2013/0273573 | A1 | 10/2013 | Allauzen et al. |
| 2014/0127128 | A1 | 5/2014 | Inagaki et al. |
| 2016/0272707 | A1 | 9/2016 | Levine et al. |
| 2016/0354315 | A1 | 12/2016 | Li |
| 2017/0181970 | A1 | 6/2017 | Tamarkin et al. |
| 2018/0021378 | A1 | 1/2018 | Kang et al. |
| 2019/0015361 | A1 | 1/2019 | Barron et al. |
| 2019/0070316 | A1 | 3/2019 | Berggren et al. |
| 2019/0374615 | A1 | 12/2019 | Kidron |
| 2023/0063416 | A1 | 3/2023 | Barron et al. |
| 2023/0355671 | A1 | 11/2023 | Barron et al. |

FOREIGN PATENT DOCUMENTS

| | | | |
|---|---|---|---|
| CN | 115461070 | A | 12/2022 |
| JP | 2010270030 | A | 12/2010 |
| WO | 2001010900 | A2 | 2/2001 |
| WO | 2004056307 | A2 | 7/2004 |
| WO | 2004058258 | A1 | 7/2004 |
| WO | 2004067025 | A1 | 8/2004 |
| WO | 2005040201 | A1 | 5/2005 |
| WO | 2009010968 | A2 | 1/2009 |
| WO | 2009026317 | A2 | 2/2009 |
| WO | 2011017600 | A2 | 2/2011 |
| WO | 2013034982 | A2 | 3/2013 |
| WO | 2014132919 | A1 | 9/2014 |
| WO | 2018175733 | A1 | 9/2018 |
| WO | 2019018445 | A1 | 1/2019 |
| WO | 2019168170 | A1 | 9/2019 |
| WO | 2021155025 | A1 | 8/2021 |
| WO | 2021188836 | A1 | 9/2021 |
| WO | 2021155025 | A8 | 3/2022 |

OTHER PUBLICATIONS

Pircher et al., "Cathelicidins prime platelets to mediate arterial thrombosis and tissue inflammation", Nature Communications, vol. 9, Article 1523, Apr. 18, 2018, 15 pgs., doi: 10.1038/s41467-018-03925-2.

Polcyn-Adamczak et al., "Cathelicidin - Its Structure, Function and The Role in Autoimmune Diseases", Advances in Cell Biology, vol. 4, No. 2, Dec. 2014, pp. 83-96, doi: 10.2478/acb-2014-0005.

Porcelli et al., "NMR Structure of the Cathelicidin-Derived Human Antimicrobial Peptide LL-37 in Dodecylphosphocholine Micelles", Biochemistry, vol. 47, No. 20, May 20, 2008, pp. 5565-5572, doi: 10.1021/bi702036s.

Pound et al., "Cathelicidin Antimicrobial Peptide: A Novel Regulator of Islet Function, Islet Regeneration, and Selected Gut Bacteria", Diabetes, vol. 64, No. 12, Dec. 2015, pp. 4135-4147, doi: 10.2337/db15-0788.

Prins et al., "NK and CD4 Cells Collaborate to Protect against Melanoma Tumor Formation in the Brain", The Journal of Immunology, vol. 177, No. 12, 2006, pp. 8448-8455, doi: 10.4049/jimmunol. 177.12.8448.

Rathod et al., "Novel insights into the effect of vitamin B12 and omega-3 fatty acids on brain function", Journal of Biomedical Science, vol. 23, No. 17, 2016, 7 pgs., doi: 10.1186/s12929-016-0241-8.

Readhead et al., "Multiscale Analysis of Independent Alzheimer's Cohorts Finds Disruption of Molecular, Genetic, and Clinical Networks by Human Herpesvirus", Neuron, vol. 99, No. 1, 2018, pp. 64-82, doi: 10.1016/j.neuron.2018.05.023.

Rekha et al., "Immune responses in the treatment of drug-sensitive pulmonary tuberculosis with phenylbutyrate and vitamin D3 as host directed therapy", BMC Infectious Diseases, vol. 18, No. 303, 2012, 12 pgs., doi: 10.1186/s12879-018-3203-9.

Rekha et al., "Phenylbutyrate induces LL-37-dependent autophagy and intracellular killing of Mycobacterium tuberculosis in human macrophages", Autophagy, vol. 11, No. 9, Sep. 2015, pp. 1688-1699, doi: 10.1080/15548627.2015.1075110.

Ricobaraza et al., "Phenylbutyrate Ameliorates Cognitive Deficit and Reduces Tau Pathology in an Alzheimer's Disease Mouse Model", Neuropsychopharmacology, vol. 34, No. 7, Jun. 2009, pp. 1721-1732, doi: 10.1038/npp.2008.229.

Ricobaraza et al., "Phenylbutyrate Rescues Dendritic Spine Loss Associated with Memory Deficits in a Mouse Model of Alzheimer Disease", Hippocampus, vol. 22, No. 5, 2012, pp. 1040-1050, doi: 10.1002/hipo.20883.

Roberts et al., "Metabolic Syndrome and Insulin Resistance: Underlying Causes and Modification by Exercise Training", Comprehensive Physiology, vol. 3, No. 1, Jan. 2013, 58 pgs., doi: 10.1002/j.2040-4603.2013.tb00484.x.

Rossi et al., "Benefits from Dietary Polyphenols for Brain Aging and Alzheimer's Disease", Neurochemical Research, vol. 33, Apr. 16, 2008, pp. 2390-2400, doi: 10.1007/s11064-008-9696-7.

Sabella et al., "Capillary electrophoresis studies on the aggregation process of B-amyloid 1-42 and 1-40 peptides", Electrophoresis, vol. 25, No. 18-19, Oct. 2004, pp. 3186-3194, doi: 10.1002/elps.200406062.

Salvado et al., "Cathelicidin LL-37 Induces Angiogenesis via PGE2-EP3 Signaling in Endothelial Cells, In Vivo Inhibition by Aspirin", Arteriosclerosis, Thrombosis, and Vascular Biology, vol. 33, No. 12, Aug. 2013, pp. 1965-1972, doi: 10.1161/ATVBAHA. 113.301851.

Sancheo-Vaello et al., "Structural remodeling and oligomerization of human cathelicidin on membranes suggest fibril-like structures as active species", Scientific Reports, vol. 7, Article 15371, Nov. 13, 2017, 11 pgs., doi: 10.1038/s41598-017-14206-1.

Sarker et al., "Treatment with Entinostat Heals Experimental Cholera by Affecting Physical and Chemical Barrier Functions of Intestinal Epithelia", Antimicrobial Agents and Chemotherapy, vol. 61, No. 7, e02570-16, 2007, 11 pgs., doi: 10.1128/AAC.02570-16.

Scarano et al., "Surface plasmon resonance imaging for affinity-based biosensors", Biosensors and Bioelectronics vol. 25, No. 5, Jan. 15, 2010, pp. 957-966, doi: 10.1016/j.bios.2009.08.039.

Schauber et al., "Expression of the cathelicidin LL-37 is modulated by short chain fatty acids in colonocytes: relevance of signalling pathways", Gut, vol. 52, No. 5, 2003, pp. 735-741, doi: 10.1136/gut.52.5.735.

Shahmiri et al., "Membrane Core-Specific Antimicrobial Action of Cathelicidin LL-37 Peptide Switches Between Pore and Nanofibre Formation", Scientific Reports, vol. 6, Article 38184, Nov. 30, 2016, 11 pgs., doi: 10.1038/srep38184.

Singh et al., "Tissue Transglutaminase Mediates Activation of RhoA and MAP Kinase Pathways during Retinoic Acid-induced Neuronal Differentiation of SH-SY5Y Cells", Journal of Biology Chemistry, vol. 278, No. 1, Jan. 3, 2003, pp. 391-399, doi: 10.1074/jbc.M206361200.

Soehnlein et al., "Neutrophil-Derived Cathelicidin Protects from Neointimal Hyperplasia", Science Translational Medicine, vol. 3, No. 103, 103ra98, 2011, 10 pgs., doi: 10.1126/scitranslmed.3002531.

Soejitno et al., "Alzheimer's Disease: Lessons Learned from Amyloidocentric Clinical Trials", CNS Drugs, vol. 29, No. 6, Jul. 18, 2015, pp. 487-502, doi: 10.1007/s40263-015-0257-8.

Soscia et al., "The Alzheimer's Disease-Associated Amyloid ß-protein is an Antimicrobial Peptide", PLOS One, vol. 5, No. 3, e9505, Mar. 3, 2010, 10 pgs., doi: 10.1371/journal.pone.0009505.

Stains et al., "Molecules that Target beta-Amyloid", ChemMedChem, vol. 2, No. 12, 2007, pp. 1675-1692, doi: 10.1002/cmdc.200700140.

Stathopulos et al., "Sonication of proteins causes formation of aggregates that resemble amyloid", Protein Science, vol. 13, No. 11, 2004, pp. 3017-3027, doi: 10.1110/ps.04831804.

Steinmann et al., "Phenylbutyrate Induces Antimicrobial Peptide Expression", Antimicrobal Agents and Chemotherapy, vol. 53, No. 12, Dec. 2009, pp. 5127-5133, doi: 10.1128/AAC.00818-09.

Stroud et al., "Toxic fibrillar oligomers of amyloid-β have cross-β structure", Proceedings of the National Academy of Sciences, vol. 109, No. 20, May 15, 2012, pp. 7717-7722, doi: 10.1073/pnas.1203193109.

Stukes et al., "Circulating Cathelicidin Concentrations in a Cohort of Healthy Children: Influence of Age, Body Composition, Gender and Vitamin D Status", Plos One, vol. 11, No. 5, May 6, 2016, 11 pgs., doi: 10.1371/journal.pone.0152711.

(56) References Cited

OTHER PUBLICATIONS

Sun et al., "Cathelicidins positively regulate pancreatic β-cell functions", The FASEB Journal, vol. 30, No. 2, 2016, pp. 884-894, doi: 10.1096/fj. 15-275826.
Sun et al., "LL-37 attenuates inflammatory impairment via mTOR signaling-dependent mitochondrial protection", The International Journal of Biochemistry & Cell Biology, vol. 54, Sep. 2014, pp. 26-35, doi: 10.1016/j.biocel.2014.06.015.
Sun et al., "Pancreatic B-Cells Limit Autoimmune Diabetes via an Immunoregulatory Antimicrobial Peptide Expressed under the Influence of the Gut Microbiota", Immunity, vol. 43, No. 2, Aug. 18, 2015, pp. 304-317, doi: 10.1016/j.immuni.2015.07.013.
Svensson et al., "Apolipoprotein A-I attenuates LL-37-induced endothelial cell cytotoxicity", Biochemical and Biophysical Research Communications, vol. 493, No. 1, Nov. 4, 2017, 6 pgs., doi: 10.1016/j.bbrc.2017.09.072.
Svensson et al., "Vitamin D-induced up-regulation of human keratinocyte cathelicidin anti-microbial peptide expression involves retinoid X receptor a", Cell and Tissue Research, vol. 366, No. 2, Jun. 30, 2016, pp. 353-362, doi: 10.1007/s00441-016-2449-z.
Tangpricha et al., "LL-37 Concentrations and the Relationship to Vitamin D, Immune Status, and Inflammation in HIV-Infected Children and Young Adults", AIDS Research and Human Retroviruses, vol. 30, No. 7, 2014, pp. 670-676, doi: 10.1089/AID.2013.0279.
Tatarek-Nossol et al., "Inhibition of hIAPP Amyloid-Fibril Formation and Apoptotic Cell Death by a Designed hIAPP Amyloid-Core-Containing Hexapeptide", Chemistry & Biology, vol. 12, No. 7, Jul. 2005, pp. 797-809, doi: 10.1016/j.chembiol.2005.05.010.
Taylor et al., "Autophagy in herpesvirus immune control and immune escape", Herpesviridae, vol. 2, No. 1, 2011, 7 pgs., doi: 10.1186/2042-4280-2-2.
Tenidis et al., "Identification of a Penta- and Hexapeptide of Islet Amyloid Polypeptide (IAPP) with Amyloidogenic and Cytotoxic Properties", Journal of Molecular Biology, vol. 295, No. 4, Jan. 28, 2000, pp. 1055-1071, doi: 10.1006/jmbi. 1999.3422.
Tripathi et al., "LL-37 modulates human neutrophil responses to influenza A Virus", Journal of Leukocyte Biology, vol. 96, No. 5, Nov. 2014, pp. 931-938, doi: 10.1189/jlb.4A1113-604RR.
Tripathi et al., "The human cathelicidin LL-37 Inhibits influenza A viruses through a mechanism distinct from that of surfactant Protein D or defensins", Journal of General Virology, vol. 94, 2013, pp. 40-49, doi: 10.1099/vir.0.045013-0.
Tsai et al., "Human Antimicrobial Peptide LL-37 Inhibits Adhesion of Candida Albicans by Interacting with Yeast Cell-Wall Carbohydrates", PLoS One, vol. 6, No. 3, e17755, Mar. 2011, 11 pgs., doi: 10.1371/journal.pone.0017755.
Van De Veerdonk et al., "Deficient autophagy unravels the ROS paradox in chronic granulomatous disease", Autophagy, vol. 10, No. 6, Jun. 2014, pp. 1141-1142, doi: 10.4161/auto.28638.
Van Der Does et al., "Induction of the human cathelicidin LL-37 as a novel treatment against bacterial infections", Journal of Leukocyte Biology, vol. 92, No. 4, Oct. 2012, pp. 735-742, doi: 10.1189/jlb.0412178.
Van Der Does et al., "Vitamin D3 and phenylbutyrate promote development of a human dendritic cell subset displaying enhanced antimicrobial properties", Journal of Leukocyte Biology, vol. 95, No. 6, 2014, pp. 883-891, doi: 10.1189/jlb. 1013549.
Vandamme et al., "A comprehensive summary of LL-37, the factotum human cathelicidin peptide", Cell Immunology, vol. 280, No. 1, Nov. 2012, pp. 22-35, doi: 10.1016/j.cellimm.2012.11.009.
Velkova et al., "Exploiting Cross-Amyloid Interactions To Inhibit Protein Aggregation but not Function: Nanomolar Affinity Inhibition of Insulin Aggregation by an IAPP Mimic", Angewandte Chemie International Edition English, vol. 47, No. 37, 2008, pp. 7114-7118, doi: 10.1002/anie.200801499.
Vercic et al., "Binding of amyloid peptides to domain-swapped dimers of other amyloid-forming proteins may prevent their neurotoxicity", Bioessays, vol. 32, No. 12, 2010, pp. 1020-1024, doi: 10.1002/bies.201000079.
Von Kockritz-Blickwede et al., "Phagocytosis-independent antimicrobial activity of mast cells by means of extracellular trap formation", Blood, vol. 111, No. 6, Mar. 15, 2008, pp. 3070-3080, doi: 10.1182/blood-2007-07-104018.
Wan et al., "Antimicrobial peptide LL-37 promotes bacterial phagocytosis by human macrophages", Journal of Leukocyte Biology, vol. 95, No. 6, Jun. 2014, pp. 971-981, doi: 10.1189/jlb.0513304.
Wan et al., "Cathelicidin LL-37 induces time-resolved release of LTB4 and TXA2 by human macrophages and triggers eicosanoid generation in vivo", The FASEB Journal, vol. 28, No. 8, Aug. 2014, pp. 3456-3467, doi: 10.1096/fj. 14-251306.
Wang et al., "Apolipoprotein A-I Binds and Inhibits the Human Antibacterial/Cytotoxic Peptide LL-37", Journal of Biological Chemistry, vol. 273, No. 50, Dec. 11, 1998, p. 33115-33118, doi: 10.1074/jbc.273.50.33115.
Wang et al., "Design of Antimicrobial Peptides: Progress Made with Human Cathelicidin LL-37", Antimicrobial Peptides, Advances in Experimental Medicine and Biology, vol. 1117, Apr. 2019, pp. 215-240, doi: 10.1007/978-981-13-3588-4_ 12.
Wang et al., "High-quality 3D structures shine light on antibacterial, anti- biofilm and antiviral activities of human cathelicidin LL-37 and its fragments", Biochimica et Biophysica Acta, vol. 1838, No. 9, Sep. 2014, pp. 2160-2172, doi: 10.1016/j.bbamem.2014.01.016.
Wang et al., "Skin Mast Cells Protect Mice Against Vaccinia Virus by Triggering Mast Cell Receptor S1PR2 and Releasing Antimicrobial Peptides", The Journal of Immunology, vol. 188, No. 1, Jan. 1, 2012, pp. 345-357, doi: 10.4049/jimmunol. 1101703.
Wang et al., "The antimicrobial peptide LL-37 binds to the human plasma protein apolipoprotein A-I", Rapid Communications Mass Spectrometry, vol. 18, No. 5, 2004, pp. 588-589, doi: 10.1002/rcm.1361.
Westermark et al., "Effects of beta cell granule components on human islet amyloid polypeptide fibril formation", FEBS Letters, vol. 379, No. 3, Feb. 5, 1996, pp. 203-206, doi: 10.1016/0014-5793(95)01512-4.
Westermark et al., "Islet Amyloid Polypeptide, Islet Amyloid, and Diabetes Mellitus", Physiological Reviews, vol. 91, No. 3, Jul. 2011, pp. 795-826, doi: 10.1152/physrev.00042.2009.
White et al., "Vitamin D as an inducer of cathelicidin antimicrobial peptide expression: past, present and future", The Journal of Steroid Biochemistry and Molecular Biology, vol. 121, No. 1-2, Jul. 2010, pp. 234-238, doi: 10.1016/j.jsbmb.2010.03.034.
Wilcox, "Insulin and Insulin Resistance", The Clinical Biochemist Reviews, vol. 26, No. 2, May 2005, pp. 19-39.
Williams et al., "Do B-Defensins and Other Antimicrobial Peptides Play a Role in Neuroimmune Function and Neurodegeneration?", The Scientific World Journal, vol. 2012, Article 905785, 2012, 11 pgs., doi: 10.1100/2012/905785.
Wiltzius et al., "Atomic structures of IAPP (amylin) fusions suggest a mechanism for fibrillation and the role of insulin in the process", Protein Science, vol. 18, No. 7, 2009, pp. 1521-1530, doi: 10.1002/pro. 145.
Wong et al., "Autophagy gone awry in neurodegenerative diseases", Nature Neuroscience, vol. 13, No. 7, Jul. 2010, pp. 805-811, doi: 10.1038/nn.2575.
Wood, "The doctor's doctor: How pathologists help diagnose disease and find the best treatment", University of Chicago Medicine, Jul. 29, 2018, 9 pgs.
Wu et al., "The Host Defense Peptide LL-37 Activates the Tumor-suppressing Bone Morphogenetic Protein Signaling Via Inhibition of Proteasome in Gastric Cancer Cells", Journal of Cellular Physiology, vol. 223, No. 1, Apr. 2010, pp. 178-186, doi: 10.1002/jcp.22026.
Xhindoli et al., "New aspects of the structure and mode of action of the human cathelicidin LL-37 revealed by the intrinsic probe p. cyanophenylalanine", Biochemical Journal, vol. 465, No. 3, Feb. 2015, pp. 443-457, doi: 10.1042/BJ20141016.
Xhindoli et al., "The human cathelicidin LL-37-A pore-forming antibacterial peptide and host-cell modulator", Biochimica et Biophysica Acta, vol. 1858, No. 3, Mar. 2016, pp. 546-566, doi: 10.1016/j.bbamem.2015.11.003.

(56) References Cited

OTHER PUBLICATIONS

Yan et al., "Design of a mimic of nonamyloidogenic and bioactive human islet amyloid polypeptide (IAPP) as nanomolar affinity inhibitor of IAPP cytotoxic fibrillogenesis", Proceedings of the National Academy of Sciences, vol. 103, No. 7, Feb. 14, 2006, pp. 2046-2051, doi: 10.1073/pnas.0507471103.
Yan et al., "IAPP Mimic Blocks AB Cytotoxic Self-Assembly: Cross- Suppression of Amyloid Toxicity of AB and IAPP Suggests a Molecular Link between Alzheimer's Disease and Type II Diabetes", Angewandte Chemie International Edition English, vol. 46, No. 8, Feb. 2007, pp. 1246-1252, doi: 10.1002/anie.200604056.
Yang et al., "LL-37, the Neutrophil Granule- and Epithelial cell-derived Cathelicidin, Utilizes Formyl Peptide Receptor-like 1 (FPRL1) as a Receptor to Chemoattract Human Peripheral Blood Neutrophils, Monocytes, and T Cells", Journal of Experimental Medicine, vol. 192, No. 7, Oct. 2, 2000, pp. 1069-1074, doi: 10.1084/jem. 192.7.1069.
Ying et al., "The role of macrophages in obesity-associated islet inflammation and ß-cell abnormalities", Nature Reviews Endocrinology, vol. 16, Feb. 2020, pp. 81-90, doi: 10.1038/s41574-019-0286-3.
Yoshimura et al., "Feasibility of Amylin Imaging in Pancreatic Islets with ß- Amyloid Imaging Probes", Scientific Reports, vol. 4, No. 6155, Aug. 21, 2014, 5 pgs., doi: 10.1038/srep06155.
Yousefi et al., "Catapult-like release of mitochondrial DNA by eosinophils contributes to antibacterial defense", Nature Medicine, vol. 14, No. 9, Sep. 2008, pp. 949-953, doi: 10.1038/nm. 1855.
Yuk et al., "Vitamin D3 Induces Autophagy in Human Monocytes/Macrophages via Cathelicidin", Cell Host & Microbe, vol. 6, No. 3, Sep. 17, 2009, pp. 231-243, doi: 10.1016/j.chom.2009.08.004.
Zandi et al., "Reduced Risk of Alzheimer Disease in Users of Antioxidant Vitamin Supplements: The Cache County Study", Archives of Neurology, vol. 61, No. 1, Jan. 2004, pp. 82-88, doi: 10.1001/archneur.61.1.82.
Zanetti, "Cathelicidins, multifunctional peptides of the innate immunity", Journal of Leukocyte Biology, vol. 75, No. 1, Jan. 2004, pp. 39-48, doi: 10.1189/jlb.0403147.
Zenaro et al., "Neutrophils promote Alzheimer's disease-like pathology and cognitive decline via LFA-1 integrin", Nature Medicine, vol. 21, No. 8, Aug. 2015, pp. 880-886, doi: 10.1038/nm.3913.
Zhang et al., "Enhanced formation and impaired degradation of neutrophil extracellular traps in dermatomyositis and polymyositis: a potential contributor to interstitial lung disease complications", Clinical and Experimental Immunology, vol. 177, No. 1, Jul. 2014, pp. 134-141, doi: 10.1111/cei.12319.
Zhang et al., "Generation of Novel Bone Forming Cells (Monoosteophils). From the Cathelicidin-Derived Peptide LL-37 Treated Monocytes", PLOS One, vol. 5, No. 11, e13985, Nov. 15, 2010, 12 pgs., doi: 10.1371/journal.pone.0013985.
Zhang et al., "The influence of cathelicidin LL37 in human anti-neutrophils cytoplasmic antibody (ANCA)-associated vasculitis", Arthritis Research & Therapy, vol. 15, No. R161, Oct. 24, 2013, 9 pgs., doi: 10.1186/ar4344.
International Preliminary Report on Patentability for International Application No. PCT/US2018/042563, Report issued Jan. 21, 2020, Mailed on Jan. 30, 2020, 45 pgs.
International Preliminary Report on Patentability for International Application No. PCT/US2021/015531, Report issued Jul. 28, 2022, Mailed Aug. 11, 2022, 6 pgs.
International Preliminary Report on Patentability for International Application No. PCT/US2021/023032, Report issued Sep. 20, 2022, Mailed on Sep. 29, 2022, 10 pgs.
International Search Report and Written Opinion for International Application No. PCT/US2018/042563, Search completed Sep. 12, 2018, Mailed Sep. 27, 2018, 11 pgs.
International Search Report and Written Opinion for International Application No. PCT/US2021/023032, Search completed Jun. 1, 2021, Mailed Jul. 1, 2021, 12 pgs.
International Search Report and Written Opinion for International Application No. PCT/US2021/015531, Search completed May 18, 2021, Mailed Jun. 30, 2021, 22 pgs.
"Barron Lab at Stanford", Available at: https://web.stanford.edu/group/barronlab/index.html., Feb. 1, 2021, 3 pgs.
"Vitamin B6, B12 & Folic Acid (B9)", Alzheimer's Drug Discovery Foundation, Jul. 13, 2016, 7 pgs.
"Vitamin D, Curcumin May Help Clear Amyloid Plaques Found In Alzheimer's Disease", Science Daily, published on Jul. 16, 2009, retrieved from internet: https://www.sciencedaily.com/releases/2009/07/090715131558.htm, retrieved on Nov. 12, 2025, 4 pgs.
Agerberth et al., "Amino acid sequence of PR-39. Isolation from pig intestine of a new member of the family of proline-arginine-rich antibacterial peptides", European Journal of Biochemistry, vol. 202, No. 3, Dec. 1991, pp. 849-854, doi: 10.1111/j. 1432-1033.1991.tb16442.x.
Agerberth et al., "Antibacterial Components in Bronchoalveolar Lavage Fluid from Healthy Individuals and Sarcoidosis Patients", American Journal of Respiratory and Critical Care Medicine. Vol. 16, No. 1, Jul. 1999, pp. 283-290, doi: 10.1164/ajrccm. 160.1.9807041.
Agerberth et al., "FALL-39, a putative human peptide Antibiotic, is cysteine-free and expressed in bone marrow and testis", Proceedings of the National Academy of Sciences, vol. 92, No. 1, Jan. 3, 1995, pp. 195-199, doi: 10.1073/pnas.92.1.195.
Agerberth et al., "The human antimicrobial and chemotactic peptides LL-37 and alpha-defensins are expressed by specific lymphocyte and monocyte populations", Blood, vol. 96, No. 9, Nov. 1, 2000, pp. 3086-3093.
Agier et al., "Cathelicidin impact on inflammatory cells", Central European Journal of Immunology, vol. 40, No. 2, 2015, pp. 225-235, doi: 10.5114/ceji.2015.51359.
Agier et al., "Cathelicidin LL-37 Affects Surface and Intracellular Toll-Like Receptor Expression in Tissue Mast Cells", Journal of Immunology Research, vol. 2018, Article 7357162, 2018, 18 pgs., doi: 10.1155/2018/7357162.
Aguilar-Jimenez et al., "Antiviral molecules correlate with vitamin D pathway genes and are associated with natural resistance to HIV-1 infection", Microbes and Infection, vol. 18, No. 7-8, Jul.-Aug. 2016, pp. 510-516, doi: 10.1016/j.micinf.2016.03.015.
Ahrens et al., "Successful in Vitro Expansion and Differentiation of Cord Blood Derived Cd34+ Cells into Early Endothelial Progenitor Cells Reveals Highly Differential Gene Expression", PLoS One, vol. 6, No. 8, e23210, Aug. 12, 2011, 12 pgs., doi: 10.1371/journal.pone.0023210.
Al-Mamun et al., "Treatment with phenylbutyrate in a pre-clinical trial reduces diarrhea due to enteropathogenic Escherichia coli: link to cathelicidin induction", Microbes and Infection, vol. 15, No. 13, Nov. 2013, pp. 939-950, doi: 10.1016/j.micinf.2013.08.007.
Andersson et al., "Isolation of human cationic antimicrobial protein-18 from seminal plasma and its association with prostasomes", Human Reproduction. Vol. 17, No. 10, Oct. 2002, pp. 2529-2534, doi: 10.1093/humrep/17.10.2529.
Andreetto et al., "A Hot-Segment-Based Approach for the Design of Cross-Amyloid Interaction Surface Mimics as Inhibitors of Amyloid Self-Assembly", Angewandte Chemie International Edition English, vol. 54, No. 44, Sep. 4, 2015, pp. 13095-13100, doi: 10.1002/anie.201504973.
Andreetto et al., "Identification of Hot Regions of the AB-IAPP Interaction Interface as High-Affinity Binding Sites in both Cross- and Self-Association", Angewandte Chemie International Edition English, vol. 49, No. 17, Apr. 12, 2010, pp. 3081-3085, doi: 10.1002/anie.200904902.
Andrieu et al., "Prevention of sporadic Alzheimer's disease: lessons learned from clinical trials and future directions", The Lancet Neurology, vol. 14, No. 9, Sep. 2015, pp. 926-944, doi: 10.1016/S1474-4422(15)00153-2.
Armiento et al., "The Human Host-Defense Peptide Cathelicidin LL-37 is a Nanomolar Inhibitor of Amyloid Self-Assembly of Islet Amyloid Polypeptide (IAPP)", Angewandte Chemie International Edition, vol. 59, No. 31, 2020, pp. 12837-12841, doi: 10.1002/anie.202000148.

(56) References Cited

OTHER PUBLICATIONS

Bakou et al., "Key aromatic/hydrophobic amino acids controlling a cross- amyloid peptide interaction versus amyloid self-assembly", Journal of Biological Chemistry, vol. 292, No. 35, Sep. 1, 2017, p. 14587-14602, doi: 10.1074/jbc.M117.774893.
Bals et al., "Cathelicidins-a family of multifunctional antimicrobial peptides", Cellular and Molecular Life Sciences CMLS, vol. 60, Apr. 2003, pp. 711-720, doi: 10.1007/s00018-003-2186-9.
Bandurska et al., "Unique features of human cathelicidin LL-37", Biofactors, vol. 41, No. 5, Sep./Oct. 2015, pp. 289-300, doi: 10.1002/biof.1225.
Barr et al., "Validation and Characterization of a Novel Peptide That Binds Monomeric and Aggregated B-Amyloid and Inhibits the Formation of Neurotoxic Oligomers", Journal of Biological Chemistry, vol. 291, No. 2, Jan. 8, 2016, pp. 547-559, doi: 10.1074/jbc.M115.679993.
Bartolini et al., "Kinetic characterization of amyloid-beta 1-42 aggregation with a multimethodological approach", Analytical Biochemistry, vol. 414, No. 2, Jul. 15, 2011, pp. 215-225.
Barwick, "Oxford University Study: High Doses of Folic Acid, Vitamin B6 and B12 Slash Brain Shrinkage By Up To 53%!", Retrieved from internet: https://www.targetednutrients.com/2016/04/18/oxford-university-study-high-doses-of-folic-acid-vitamin-b6-and-b12-slash-brain-shrinkage-by-up-to-53/, retrieved on Nov. 12, 2025, 3 pgs.
Benachour et al., "Association of human cathelicidin (hCAP-18/LL-37) gene expression with cardiovascular disease risk factors", Nutrition, Metabolism and Cardiovascular Diseases, vol. 19, No. 10, Dec. 2009, pp. 720-728, doi: 10.1016/j.numecd.2009.01.001.
Bergman et al., "The Antimicrobial Peptide LL-37 Inhibits HIV-1 Replication", Current HIV Research, vol. 5, No. 4, 2007, pp. 410-415, doi: 10.2174/157016207781023947.
Bilkei-Gorzo, "Genetic mouse models of brain ageing and Alzheimer's disease", Pharmacology & Therapeutics, vol. 142, No. 2, May 2014, pp. 244-257, doi: 10.1016/j.pharmthera.2013.12.009.
Block et al., "Microglia-mediated neurotoxicity: uncovering the molecular mechanisms", Nature Reviews Neuroscience, vol. 8, No. 1, Jan. 1, 2007, pp. 57-69, doi: 10.1038/nrn2038.
Boman et al., "Mechanisms of Action on Escherichia Coli of Cecropin P1 and Pr-39, Two Antibacterial Peptides from Pig Intestine", Infection and Immunity, vol. 61, No. 7, Jul. 1993, pp. 2978-2984, doi: 10.1128/iai.61.7.2978-2984. 1993.
Bourgade et al., "B-Amyloid peptides display protective activity against the human Alzheimer's disease-associated herpes simplex virus-1", Biogerontology, vol. 16, 2015, pp. 85-98, doi: 10.1007/s10522-014-9538-8.
Brinkmann et al., "Beneficial suicide: why neutrophils die to make NETs", Nature Reviews Microbiology, vol. 5, Aug. 2007, pp. 577-582, doi: 10.1038/nrmicro1710.
Brogi et al., "Disease-Modifying Anti-Alzheimer's drugs: Inhibitors of Human Cholinesterases Interfering with ß-Amyloid Aggregation", CNS Neuroscience and Therapeutics, vol. 20, No. 7, Jul. 2014, pp. 624-632, doi: 10.1111/cns. 12290.
Bruns et al., "Vitamin D-dependent induction of cathelicidin in human macrophages results in cytotoxicity against high-grade B cell lymphoma", Science Translational Medicine, vol. 7, No. 282, Apr. 8, 2015, 13 pgs., doi: 10.1126/scitranslmed.aaa3230.
Büchau et al., "The Host Defense Peptide Cathelicidin Is Required for NK Cell-Mediated Suppression of Tumor Growth", The Journal of Immunology, vol. 184, No. 1, Jan. 2010, pp. 369-378, do: 10.4049/jimmunol.0902110.
Bucki et al., "Cathelicidin LL-37: A Multitask Antimicrobial Peptide", Archivum Immunologiae et Therapiae Experimentalis, vol. 58, 2010, pp. 15-25, doi: 10.1007/s00005-009-0057-2.
Burton et al., "The chemistry and biology of LL-37", Natural Product Reports, vol. 26, No. 12, 2009, pp. 1572-1584, 2009, doi: 10.1039/b912533g.
Butini et al., "Multifunctional Cholinesterase and Amyloid Beta Fibrillization Modulators. Synthesis and Biological Investigation", ACS Medicinal Chemistry Letters, vol. 4, No. 12, Oct. 6, 2013, pp. 1178-1182, doi: 10.1021/ml4002908.
Byfield et al., "Cathelicidin LL-37 Increases Lung Epithelial Cell Stiffness, Decreases Transepithelial Permeability, and Prevents Epithelial Invasion by Pseudomonas Aeruginosa", The Journal of Immunology, vol. 187, No. 12, Dec. 2011, pp. 6402-6409, doi: 10.4049/jimmunol.1102185.
Byfield et al., "Cathelicidin LL-37 peptide regulates endothelial cell stiffness and endothelial barrier permeability", American Journal of Physiology-Cell Physiology, vol. 300, No. 1, Jan. 2011, pp. C105-C112, doi: 10.1152/ajpcell.00158.2010.
Casali et al., "Omega-3 Fatty Acids Augment the Actions of Nuclear Receptor Agonists in a Mouse Model of Alzheimer's Disease", Journal of Neuroscience, vol. 35, No. 24, Jun. 17, 2015, pp. 9173-9181, doi: 10.1523/JNEUROSCI.1000-15.2015.
Cederlund et al., "Label-Free Quantitative Mass Spectrometry Reveals Novel Pathways Involved in LL-37 Expression", Journal of Innate Immunity, vol. 6, No. 3, 2014, pp. 365-376, doi: 10.1159/000355931.
Champeau, "Vitamin D, curcumin may help clear amyloid plaques found In Alzheimer's", UCLA Newsroom, Science & Technology, published on Jul. 15, 2009, retrieved from internet: https://www.uclahealth.org/news/release/vitamin-d-curcumin-may-help-clear-amyloid-plaques-found-in-alzheimers, retrieved on Nov. 12, 2025, 2 pgs.
Chen et al., "A combinational therapy of EGFR-CAR NK cells and oncolytic herpes simplex virus 1 for breast cancer brain metastases", Oncotarget, vol. 7, No. 19, Apr. 1, 2016, p. 27764-2777, doi: 10.18632/oncotarget.8526.
Chen et al., "A new class of hybrid anticancer agents inspired by the synergistic effects of curcumin and genistein: Design, synthesis, and anti-proliferative evaluation", Bioorganic & Medicinal Chemistry Letters, vol. 25, No. 20, Oct. 15, 2015, pp. 4553-4556, doi: 10.1016/j.bmcl.2015.08.064.
Chen et al., "Human antimicrobial peptide LL-37 contributes to Alzheimer's disease progression", Molecular Psychiatry, vol. 27, No. 11, 2022, pp. 4790-4799, doi: 10.1038/s41380-022-01790-6.
Chongsiriwatana et al., "Intracellular biomass flocculation as a key mechanism of rapid bacterial killing by cationic, amphipathic antimicrobial peptides and peptoids", Scientific Reports, vol. 7, Article 16718, Dec. 1, 2017, 15 pgs., doi: 10.1038/s41598-017-16180-0.
Chromek et al., "The antimicrobial peptide cathelicidin protects the urinary tract against invasive bacterial infection", Nature Medicine, vol. 12, No. 6, Jun. 2006, pp. 636-641, doi: 10.1038/nm1407.
Chuang et al., "Treatment with LL-37 Peptide Enhances Antitumor Effects Induced by CpG Oligodeoxynucleotides Against Ovarian Cancer", Human Gene Therapy, vol. 20, No. 4, Apr. 2009, pp. 303-313, doi: 10.1089/hum.2008.124.
Ciornei et al., "Human antimicrobial peptide LL-37 is present in atherosclerotic plaques and induces death of vascular smooth muscle cells: a laboratory study", BMC Cardiovascular Disorders, No. 6, Article 49, Dec. 20, 2006, 12 pgs., doi: 10.1186/1471-2261-6-49.
Coffelt et al., "Ovarian cancers overexpress the antimicrobial protein hCAP-18 and its derivative LL-37 increases ovarian cancer cell proliferation and invasion", International Journal of Cancer, vol. 122, No. 5, Dec. 24, 2007, pp. 1030-1039, doi: 10.1002/ijc.23186.
Cohen et al., "A molecular chaperone breaks the catalytic cycle that generates toxic AB oligomers", Nature Structural & Molecular Biology, vol. 22, No. 3, 2015, pp. 207-213, doi: 10.1038/nsmb.2971.
Cohen et al., "Proliferation of amyloid-β42 aggregates occurs through a secondary nucleation mechanism", Proceedings of the National Academy of Sciences, vol. 110, No. 24, Jun. 11, 2013, pp. 9758-9763, doi: 10.1073/pnas. 1218402110.
Colombo et al., "CE can identify small molecules that selectively target soluble oligomers of amyloid ß protein and display antifibrillogenic activity", Electrophoresis, vol. 30, No. 8, Apr. 2009, pp. 1418-1429, doi: 10.1002/elps.200800377.
Cretich et al., "Overcoming mass transport limitations to achieve femtomolar detection limits on silicon protein microarrays", Analytical Biochemistry, vol. 418, No. 1, Nov. 1, 2011, pp. 164-166, doi: 10.1016/j.ab.2011.07.004.

(56) References Cited

OTHER PUBLICATIONS

Cui et al., "Potential role of the formyl peptide receptor-like 1 (FPRL1) in inflammatory aspects of Alzheimer's disease", Journal of Leukocyte Biology, vol. 72, No. 4, Oct. 2002, pp. 628-635, doi: 10.1189/jlb.72.4.628.
Currais et al., "Amyloid proteotoxicity initiates an inflammatory response blocked by cannabinoids", Japanese Society of Anti-Aging Mechanisms of Disease, vol. 2, Article 16012, 2016, 8 pgs., doi: 10.1038/npjamd.2016.12.
Currie et al., "Cathelicidins Have Direct Antiviral Activity against Respiratory Syncytial Virus In Vitro and Protective Function In Vivo in Mice and Humans", Journal of Immunology, vol. 196, No. 6, Mar. 2016, pp. 2699-2710, doi: 10.4049/jimmunol. 1502478.
Davison et al., "Salivary antimicrobial peptides (LL-37 and alpha-defensins HNP1-3), antimicrobial and IgA responses to prolonged exercise", European Journal of Applied Physiology, vol. 106, No. 2, Mar. 5, 2009, pp. 277-284, doi: 10.1007/s00421-009-1020-y.
De La Monte, "Type 3 Diabetes is Sporadic Alzheimers disease: Mini-Review", European Neuropsychopharmacology, vol. 24, No. 12, Dec. 2014, pp. 1954-1960, doi: 10.1016/j.euroneuro.2014.06.008.
De La Monte et al., "Alzheimer's Disease Is Type 3 Diabetes-Evidence Reviewed", Journal of Diabetes Science and Technology, vol. 2, No. 6, Nov. 2008, pp. 1101-1113, doi: 10.1177/193229680800200619.
De Lorenzi et al., "Evidence that the Human Innate Immune Peptide LL-37 may be a Binding Partner of Amyloid-B and Inhibitor of Fibril Assembly", Journal of Alzheimer's Disease, vol. 59, No. 4, 2017, pp. 1213-1226, doi: 10.3233/JAD-170223.
Dorschner et al., "Cutaneous Injury Induces the Release of Cathelicidin Anti-Microbial Peptides Active Against Group A Streptococcus", Journal of Investigative Dermatology, vol. 117, No. 1, Jul. 2001, pp. 91-97, doi: 10.1046/j. 1523-1747.2001.01340.x.
Douaud et al., "Preventing Alzheimer's disease-related gray matter atrophy by B-vitamin treatment", Proceedings of the National Academy of Sciences, vol. 110, No. 23, Jun. 4, 2013, pp. 9523-9528, doi: 10.1073/pnas. 1301816110.
Durk et al., "1α,25-Dihydroxyvitamin D3 Reduces Cerebral Amyloid-β Accumulation and Improves Cognition in Mouse Models of Alzheimer's Disease", Journal of Neuroscience, vol. 34, No. 21, May 21, 2014, pp. 7091-7101, doi: 10.1523/JNEUROSCI.2711-13.2014.
Durr et al., "LL-37, the only human member of the cathelicidin family of antimicrobial peptides", Biochimica et Biophysica Acta, vol. 1758, No. 9, Sep. 2006, pp. 1408-1425, doi: 10.1016/j.bbamem.2006.03.030.
Edfeldt et al., "Involvement of the Antimicrobial Peptide LL-37 in Human Atherosclerosis", Arteriosclerosis, Thrombosis, and Vascular Biology, vol. 26, No. 7, 2006, pp. 1551-1557, doi: 10.1161/01.ATV.0000223901.08459.57.
Eimer et al., "Alzheimer's Disease-Associated B-Amyloid Is Rapidly Seeded by Herpesviridae to Protect against Brain Infection", Neuron, vol. 99, No. 1, Jul. 11, 2018, pp. 56-63, doi: 10.1016/j.neuron.2018.06.030.
Eimer et al., "Neuron loss in the 5XFAD mouse model of Alzheimer's disease correlates with intraneuronal Aß42 accumulation and Caspase-3 activation", Molecular Neurodegeneration, vol. 8, Article 2, 2013, 12 pgs., doi: 10.1186/1750-1326-8-2.
Fahy et al., "Pulmonary Defense and the Human Cathelicidin hCAP-18/LL- 37", Immunologic Research, vol. 31, No. 2, Mar. 2005, pp. 75-89, doi: 10.1385/IR:31:2:075.
Fernando et al., "The role of dietary coconut for the prevention and treatment of Alzheimer's disease: potential mechanisms of action", British Journal of Nutrition, vol. 114, No. 1, 2015, 14 pgs., doi: 10.1017/S0007114515001452.
Frank, "The SPOT-synthesis technique: Synthetic peptide arrays on membrane supports-principles and applications", Journal of Immunological Methods, vol. 267, No. 1, Sep. 1, 2002, pp. 13-26, doi: 10.1016/s0022-1759(02)00137-0.
Frohm et al., "The Expression of the Gene Coding for the Antibacterial Peptide LL-37 is Induced in Human Keratinocytes During Inflammatory Disorders", Journal of Biological Chemistry, vol. 272, No. 24, Jun. 13, 1997, p. 15258-15263, doi: 10.1074/jbc.272.24.15258.
Ganai et al., "Bioactivity of genistein: A review of in vitro and in vivo studies", Biomedicine and Pharmacotherapy, vol. 76, Dec. 2015, pp. 30-38, doi: 10.1016/j.biopha.2015.10.026.
Garcia-Alloza et al., "Curcumin labels amyloid pathology in vivo, disrupts existing plaques, and partially restores distorted neurites in an Alzheimer mouse model", Journal of Neurochemistry, vol. 102, Aug. 2007, pp. 1095-1104, doi: 10.1111/j. 1471-4159.2007.04613.x.
Garcia-Romo et al., "Netting Neutrophils are Major Inducers of Type I IFN Production in Pediatric Systemic Lupus Erythematosus", Science Translational Medicine, vol. 3, No. 73, Article 73ra20, Mar. 9, 2011, 13 pgs., doi: 10.1126/scitranslmed.3001201.
Gauthier et al., "Targeting Alzheimer's Disease at the Right Time and the Right Place: Validation of a Personalized Approach to Diagnosis and Treatment", Journal of Alzheimer's Disease, vol. 64, No. 1, 2018, pp. S23-S31, doi: 10.3233/JAD-179924.
Ginsberg et al., "The Obesity, Metabolic Syndrome, and Type 2 Diabetes Mellitus Pandemic: Part I. Increased Cardiovascular Disease Risk and the Importance of Atherogenic Dyslipidemia in Persons With the Metabolic Syndrome and Type 2 Diabetes Mellitus", Journal of the Cardiometabolic Syndrome, vol. 4, No. 2, 2009, pp. 113-119, doi: 10.1111/j.1559-4572.2008.00044.x.
Goedert, "Alzheimer's and Parkinson's diseases: The prion concept in relation to assembled AB, tau, and a-synuclein", Science, vol. 349, No. 6248, Aug. 2015, p. 1255555-1 - 1255555-9, doi: 10.1126/science. 1255555.
Gombart et al., "Exaptation of an ancient Alu short interspersed element provides a highly conserved vitamin D-mediated innate immune response in humans and primates", BMC Genomics, vol. 10, Article 321, 2009, 11 pgs., doi: 10.1186/1471-2164-10-321.
Gombart et al., "Human cathelicidin antimicrobial peptide (CAMP) gene is a direct target of the vitamin D receptor and is strongly up-regulated in myeloid cells by 1,25- dihydroxyvitamin D3", Faseb Journal, vol. 19, No. 9, Jul. 2005, pp. 1067-1077, doi: 10.1039/b912533g.
Gombart et al., "Regulation of the CAMP gene by 1, 25 (OH) 2D3 in various tissues", The Journal of Steroid Biochemistry and Molecular Biology, vol. 103, No. 3-5, Mar. 2007, pp. 552-557, doi: 10.1016/j.jsbmb.2006.12.095.
Gordon et al., "Human Cathelicidin (LL-37), a Multifunctional Peptide, is Expressed by Ocular Surface Epithelia and has Potent Antibacterial and Antiviral Activity", Current Eye Research, vol. 30, 2005, pp. 385-394, doi: 10.1080/02713680590934111.
Gudmundsson et al., "The human gene FALL39 and processing of the cathelin precursor to the antibacterial peptide LL-37 in granulocytes", European Journal of Biochemistry, vol. 228, No. 2, Jun. 1996, pp. 325-332, doi: 10.1111/j.1432-1033.1996.0325z.x.
Guo et al., "Curcumin induces human cathelicidin antimicrobial peptide gene expression through a vitamin D receptor-independent pathway", Journal of Nutritional Biochemistry, vol. 24, No. 5, May 2013, pp. 754-759, doi: 10.1016/j.jnutbio.2012.04.002.
Guo et al., "Synergistic induction of human cathelicidin antimicrobial peptide gene expression by vitamin D and stilbenoids", Molecular Nutrition & Food Research, vol. 58, No. 3, Mar. 2014, pp. 528-536, doi: 10.1002/mnfr.201300266.
Hase et al., "Expression of LL-37 by Human Gastric Epithelial Cells as a Potential Host Defense Mechanism Against Helicobacter pylori", Gastroenterology, vol. 125, No. 6, Dec. 2003, pp. 1613-1625, doi: 10.1053/j.gastro.2003.08.028.
Heilborn et al., "Antimicrobial protein hCAP18/LL-37 is highly expressed in breast cancer and is a putative growth factor for epithelial cells", International Journal of Cancer, vol. 114, No. 5, 2005, pp. 713-719, doi: 10.1002/ijc.20795.
Hemshekhar et al., "Immunomodulatory Functions of the Human Cathelicidin LL-37 (aa 13-31)-Derived Peptides are Associated with Predicted α-Helical Propensity and Hydrophobic Index", Biomolecules, vol. 9, No. 501, 2019, 15 pgs., doi: 10.3390/biom9090501.

(56) References Cited

OTHER PUBLICATIONS

Hertting et al., "Vitamin D Induction of the Human Antimicrobial Peptide Cathelicidin in the Urinary Bladder", PLOS One, vol. 5, No. 12, Article e15580, Dec. 14, 2010, 9 pgs., doi: 10.1371/journal.pone.0015580.

Hou et al., "Chlamydial plasmid-encoded virulence factor Pgp3 interacts with human cathelicidin peptide LL-37 to modulate immune response", Microbes and Infection, vol. 21, No. 1, Jan.-Feb. 2019, pp. 50-55, doi: 10.1016/j.micinf.2018.06.003.

Howell et al., "Cathelicidin deficiency predisposes to eczema herpeticum", Journal of Allergy and Clinical Immunology, vol. 117, No. 4, Apr. 2006, pp. 836-841, doi: 10.1016/j.jaci.2005.12.1345.

Huang et al., "A Time-Efficient, Linear-Space Local Similarity Algorithm", Advances in Applied Mathematics, vol. 12, No. 3, Sep. 1991, pp. 337-357, doi: 10.1016/0196-8858(91)90017-D.

Huang et al., "Alzheimer Mechanisms and Therapeutic Strategies", Cell, vol. 148, No. 6, Mar. 16, 2012, pp. 1204-1222, doi: 10.1016/j.cell.2012.02.040.

Ilievski et al., "Chronic oral application of a periodontal pathogen results in brain inflammation, neurodegeneration and amyloid beta production in wild type mice", Plos One, vol. 13, No. 10, Oct. 3, 2018, 24 pgs., doi: 10.1371/journal.pone.0204941.

Iribarren et al., "Role of Formyl Peptide Receptor- Like 1 (FPRL1/FPR2) in Mononuclear Phagocyte Responses in Alzheimer Disease", Immunological Research, vol. 31, No. 3, Apr. 2005, pp. 165-176, doi: 10.1385/IR:31:3:165.

Jeong et al., "Sphingosine kinase 1 activation enhances epidermal innate immunity through sphingosine-1-phosphate stimulation of cathelicidin production", Journal of Dermatological Science, vol. 79, No. 3, Sep. 2015, pp. 229-234, doi: 10.1016/j.jdermsci.2015.06.007.

Johansson et al., "Conformation-dependent Antibacterial Activity of the Naturally Occurring Human Peptide LL-37", The Journal of Biological Chemistry, vol. 273, No. 6, Feb. 1, 1998, pp. 3718-3724, doi: 10.1074/jbc.273.6.3718.

Kai et al., "Tabersonine inhibits amyloid fibril formation and cytotoxicity of Aβ(1-42)", Acs Chemical Neuroscience, vol. 6, No. 6, Apr. 15, 2015, pp. 879-888, doi: 10.1021/acschemneuro.5b00015.

Kapurniotu et al., "Structure-Based Design and Study of Non-amyloidogenic, Double N-Methylated IAPP Amyloid Core Sequences as Inhibitors of IAPP Amyloid Formation and Cytotoxicity", Journal of Molecular Biology, vol. 315, No. 3, Jan. 18, 2002, pp. 339-350, doi: 10.1006/jmbi.2001.5244.

Karuppagounder et al., "Dietary supplementation with resveratrol reduces plaque pathology in a transgenic model of Alzheimer's disease", Neurochemistry International, vol. 54, No. 2, Feb. 2009, pp. 111-118, doi: 10.1016/j.neuint.2008.10.008.

Katz et al., "Studying protein-protein interactions using peptide arrays", Chemical Society Reviews, vol. 40, No. 5, May 2011, pp. 2131-2145, doi: 10.1039/c0cs00029a.

Kayed et al., "Common Structure of Soluble Amyloid Oligomers Implies Common Mechanism of Pathogenesis", Science, vol. 300, No. 5618, Apr. 18, 2003, pp. 486-489, doi: 10.1126/science. 1079469.

Kayed et al., "Conformational Transitions of Islet Amyloid Polypeptide (IAPP) in Amyloid Formation in Vitro", Journal of Molecular Biology, vol. 287, No. 4, Apr. 9, 1999, pp. 781-796, doi: 10.1006/jmbi. 1999.2646.

Kazantzis et al., "Conformationally constrained human calcitonin (hCt) analogues reveal a critical role of sequence 17-21 for the oligomerization state and bioactivity of hCt", European Journal of Biochemistry, vol. 269, No. 3, Feb. 2002, pp. 780-791, doi: 10.1046/j.0014-2956.2001.02689.x.

Khan et al., "Effect of Curcumin and Vitamin D3 on Learning and Cognition Inrat Model of Alzheimer's Disease", Austin Journal of Cerebrovascular Disease & Stroke, vol. 4, No. 3, Jun. 7, 2017, 5 pgs., doi: 10.26420/austinjcerebrovascdisstroke.2017.1060.

Kida et al., "Sodium butyrate up-regulates cathelicidin gene expression via activator protein-1 and histone acetylation at the promoter region in a human lung epithelial cell line, EBC-1", Molecular Immunology, vol. 43, No. 12, May 2006, pp. 1972-1981, doi: 10.1016/j.molimm.2005.11.014.

Kim et al., "The antimicrobial peptide human cationic antimicrobial protein-18/cathelicidin LL-37 as a putative growth factor for malignant melanoma", British Journal of Dermatology, vol. 163, No. 5, Nov. 1, 2010, pp. 959-967, doi: 10.1111/j.1365-2133.2010.09957.x.

Kokkoni et al., "N-Methylated Peptide Inhibitors of β-Amyloid Aggregation and Toxicity. Optimization of the Inhibitor Structure", Biochemistry, vol. 45, No. 32, Jul. 25, 2006, pp. 9906-9918, doi: 10.1021/bi060837s.

Kroth et al., "Discovery and Structure Activity Relationship of Small Molecule Inhibitors of Toxic β-Amyloid-42 Fibril Formation", The Journal of Biological Chemistry, vol. 287, No. 41, Oct. 5, 2012, p. 34786-34800, doi: 10.1074/jbc.M112.357665.

Kulkarni et al., "Phenylbutyrate induces cathelicidin expression via the vitamin D receptor: Linkage to inflammatory and growth factor cytokines pathways", Molecular Immunology, vol. 63, No. 2, Feb. 2015, pp. 530-539, doi: 10.1016/j.molimm.2014.10.007.

Kumar et al., "Amyloid-ß peptide protects against microbial infection in mouse and worm models of Alzheimer's disease", Science Translational Medicine, vol. 8, No. 340, Article 340ra72, May 25, 2016, 15 pgs., doi: 10.1126/scitranslmed.aaf1059.

Lacy et al., "Identification of an Arg-Leu-Arg tripeptide that contributes to the binding interface between the cytokine MIF and the chemokine receptor CXCR4", Scientific Reports, vol. 8, No. 1, Article 5171, Mar. 26, 2018, 1 pg., doi: 10.1038/s41598-018-23554-5.

Ladiwala et al., "Aromatic Small Molecules Remodel Toxic Soluble Oligomers of Amyloid ß through Three Independent Pathways", The Journal of Biological Chemistry, vol. 286, No. 5, Feb. 4, 2011, pp. 3209-3218, doi: 10.1074/jbc.M110.173856.

Lai et al., "Vitamin D supplementation worsens Alzheimer's progression: Animal model and human cohort studies", Aging Cell, vol. 21, 2022, 13 pgs., doi: 10.1111/acel. 13670.

Lande et al., "Neutrophils Activate Plasmacytoid Dendritic Cells by Releasing Self-DNA-Peptide Complexes in Systemic Lupus Erythematosus", Science Translational Medicine, vol. 3, No. 73, Article 73ra19, Mar. 9, 2011, 11 pgs., doi: 10.1126/scitranslmed.3001180.

Lande et al., "Plasmacytoid dendritic cells sense self-DNA coupled with antimicrobial peptide", Nature, vol. 449, Oct. 4, 2007, pp. 564-569, doi: 10.1038/nature06116.

Larrick et al., "Human CAP18: a Novel Antimicrobial Lipopolysaccharide-Binding Protein", Infection and Immunity, vol. 63, No. 4, Apr. 1995, pp. 1291-1297, doi: 10.1128/iai.63.4.1291-1297.1995.

Lau et al., "Apoptosis of Airway Epithelial Cells: Human Serum Sensitive Induction by the Cathelicidin LL-37", American Journal of Respiratory Cell and Molecular Biology, vol. 34, No. 4, 2006, pp. 399-409, doi: 10.1165/rcmb.2005-01700C.

Lau et al., "Synthesis of a Model Protein of Defined Secondary and Quaternary Structure Effect of Chain Length on the Stabilization and Formation of Two-Stranded a-Helical Coiled-Coils", The Journal of Biological Chemistry, vol. 259, No. 21, Nov. 10, 1984, pp. 13253-13261, doi: 10.1016/s0021-9258(18)90686-1.

Lauth et al., "M1 Protein Allows Group A Streptococcal Survival in Phagocyte Extracellular Traps through Cathelicidin Inhibition", Journal of Innate Immunity, vol. 1, 2009, pp. 202-214, doi: 10.1159/000203645.

Le et al., "Amyloid β42 Activates a G-Protein-Coupled Chemoattractant Receptor, FPR-Like-1", Journal of Neuroscience, vol. 21, Article RC123, Jan. 15, 2001, 5 pgs., doi: 10.1523/JNEUROSCI.21-02-j0003.2001.

Lee et al., "Acidic Fibroblast Growth Factor (FGF) Potentiates Glial-mediated Neurotoxicity by activating FGFR2 IIlb Protein", The Journal of Biological Chemistry, vol. 286, No. 48, Dec. 2, 2011, p. 41230-41245, doi: 10.1074/jbc.M111.270470.

Lee et al., "Depletion of GSH in glial cells induces neurotoxicity: relevance to aging and degenerative neurological diseases", The FASEB Journal, vol. 24, Jul. 2010, pp. 2533-2545, doi: 10.1096/fj.09-149997.

Lee et al., "Human antimicrobial peptide LL-37 induces glial-mediated neuroinflammation", Biochemical Pharmacology, vol. 94, No. 2, Mar. 15, 2015, pp. 130-141, doi: 10.1016/j.bcp.2015.02.003.

(56) References Cited

OTHER PUBLICATIONS

Lee et al., "Metabolic Syndrome", Pediatrics in Review, vol. 33, No. 10, Oct. 2012, pp. 459-468, doi: 10.1542/pir.33-10-459.
Lee et al., "Natural killer (NK) cells inhibit systemic metastasis of glioblastoma cells and have therapeutic effects against glioblastomas in the brain", BMC Cancer, vol. 15, No. 1011, Dec. 24, 2015, 13 pgs., doi: 10.1186/s12885-015-2034-y.
Lee et al., "Neurotoxins Released from Interferon-Gamma-Stimulated Human Astrocytes", Neuroscience, vol. 229, Jan. 15, 2013, pp. 164-175, doi: 10.1016/j.neuroscience.2012.10.033.
Li et al., "Multifunctional in vivo imaging of pancreatic islets during diabetes development", Journal of Cell Science, vol. 129, Jul. 15, 2016, pp. 2865-2875, doi: 10.1242/jcs. 190843.
Lim et al., "Chlamydia pneumoniae infection of monocytes in vitro stimulates innate and adaptive immune responses relevant to those in Alzheimer's disease", Journal of Neuroinflammation, vol. 11, No. 217, Dec. 24, 2014, 11 pgs., doi: 10.1186/s12974-014-0217-0.
Linde et al., "Clinical Relevance of Cathelicidin in Infectious Disease", Journal of Clinical Cell Immunology, vol. S13, Mar. 31, 2013, 11 pgs., doi: 10.4172/2155-9899.S13-003.
Lopez-Garcia et al., "Anti-Fungal Activity of Cathelicidins and their Potential Role in Candida albicans Skin Infection", The Journal of Investigative Dermatology, vol. 125, Jul. 2005, pp. 108-115, doi: 10.1111/j.0022- 202X.2005.23713.x.
Lowry et al., "Regulation of the human cathelicidin antimicrobial peptide gene by 1a,25-dihydroxyvitamin D3 in primary immune cells", The Journal of Steroid Biochemistry and Molecular Biology, vol. 143, Sep. 2014, pp. 183-191, doi: 10.1016/j.jsbmb.2014.02.004.
Luo et al., "Cross-interactions between the Alzheimer Disease Amyloid-β Peptide and Other Amyloid Proteins: A Further Aspect of the Amyloid Cascade Hypothesis", The Journal of Biological Chemistry, vol. 291, No. 32, Aug. 5, 2016, p. 16485-16493, doi: 10.1074/jbc.R116.714576.
Maarouf et al., "Molecular Differences and Similarities Between Alzheimer's Disease and the 5XFAD Transgenic Mouse Model of Amyloidosis", Biochemistry Insights, vol. 6, Nov. 21, 2013, 10 pgs., doi: 10.4137/BCI.S13025.
Mader et al., "The Human Host Defense Peptide LL-37 Induces Apoptosis in a Calpain- and Apoptosis-Inducing Factor-Dependent Manner Involving Bax Activity", Molecular Cancer Research, vol. 7, No. 5, May 2009, pp. 689-702, doi: 10.1158/1541-7786.MCR-08-0274.
Maheshwari et al., "Bacterial Infection and Alzheimer's Disease: A Meta-Analysis", Journal of Alzheimer's disease, vol. 43, 2015, pp. 957-966, doi: 10.3233/JAD-140621.
Marchini et al., "The newborn infant is protected by an innate antimicrobial barrier: peptide antibiotics are present in the skin and vernix caseosa", The British Journal of Dermatology, vol. 147, No. 6, Dec. 2002, pp. 1127-1134, doi: 10.1046/j. 1365-2133.2002.05014.x.
Mariani et al., "Neuronally-directed effects of RXR activation in a mouse model of Alzheimer's disease", Scientific Reports, vol. 7, No. 42270, Feb. 16, 2017, 12 pgs., doi: 10.1038/srep42270.
Marino et al., "Autophagy for tissue homeostasis and neuroprotection", Current Opinion in Cell Biology, vol. 23, No. 2, Apr. 2011, pp. 198-206, doi: 10.1016/j.ceb.2010.10.001.
Masters et al., "Activation of the NLRP3 inflammasome by islet amyloid polypeptide provides a mechanism for enhanced IL-1β in type 2 diabetes", Nature Immunology, vol. 11, No. 10, Oct. 2010, pp. 897-904, doi: 10.1038/ni. 1935.
Matsumura et al., "Antimicrobial peptide LL-37 attenuates infection of hepatitis C virus", Hepatology Research, vol. 46, No. 9, Nov. 26, 2015, pp. 924-932, doi: 10.1111/hepr. 12627.
Mawuenyega et al., "Decreased Clearance of CNS β-Amyloid in Alzheimer's Disease", Science, vol. 330. No. 6012, Dec. 24, 2010, p. 1774, doi: 10.1126/science. 1197623.
Mayer et al., "Cathelicidins Link the Endocrine and Immune Systems", Cell Host and Microbe, vol. 7, No. 4, Apr. 22, 2010, pp. 257-259, doi: 10.3390/vaccines6030063.
Merlini et al., "Molecular Mechanisms of Amyloidosis", The New England Journal of Medicine, vol. 349, No. 6, Aug. 7, 2003, pp. 583-596, doi: 10.1056/NEJMra023144.
Merres et al., "Role of the Cathelicidin-Related Antimicrobial Peptide in Inflammation and Mortality in a Mouse Model of Bacterial Meningitis", Journal of Innate Immunity, vol. 6, No. 2, 2013, pp. 205-218, doi: 10.1159/000353645.
Miklossy, "Bacterial Amyloid and DNA are Important Constituents of Senile Plaques: Further Evidence of the Spirochetal and Biofilm Nature of Senile Plaques", Journal of Alzheimer's Disease, vol. 53, No. 4, Jun. 13, 2016, pp. 1459-1473, doi: 10.3233/JAD-160451.
Miklossy, "Historic evidence to support a causal relationship between spirochetal infections and Alzheimer's disease", Frontiers in Aging Neuroscience, vol. 7, Article 46, Apr. 16, 2015, 12 pgs., doi: 10.3389/fnagi.2015.00046.
Mily et al., "Oral intake of phenylbutyrate with or without vitamin D3 upregulates the cathelicidin LL-37 in human macrophages: a dose finding study for treatment of tuberculosis", BMC Pulmonary Medicine, vol. 13, No. 23, 2013, 8 pgs., doi: 10.1186/1471-2466-13-23.
Mily et al., "Significant Effects of Oral Phenylbutyrate and Vitamin D3 Adjunctive Therapy in Pulmonary Tuberculosis: A Randomized Controlled Ttrial", PLoS One, vol. 10, No. 9, Sep. 22, 2015, 25 pgs., doi: 10.1371/journal.pone.0138340.
Minetto et al., "Harnessing NK Cells for Cancer Treatment", Frontiers in Immunology, vol. 10, Article 2836, Dec. 6, 2019, 10 pgs., doi: 10.3389/fimmu.2019.02836.
Miraglia et al., "Entinostat up-regulates the CAMP gene encoding LL-37 via activation of STAT3 and HIF-1α transcription factors", Scientific Reports, vol. 6, No. 33274, Sep. 16, 2016, 12 pgs., doi: 10.1038/srep33274.
Mizwicki et al., "Genomic and Nongenomic Signaling Induced by 1a,25(OH)2-Vitamin D3 Promotes the Recovery of Amyloid-ß Phagocytosis by Alzheimer's Disease Macrophages", Journal of Alzheimer's Disease, vol. 29, No. 1, Mar. 2, 2012, pp. 51-62, doi: 10.3233/JAD-2012-11056.
Mookherjee et al., "Systems biology evaluation of immune responses induced by human host defence peptide LL-37 in mononuclear cells", Molecular BioSystems, vol. 5, No. 5, 2009, pp. 483-496, doi: 10.1039/b813787k.
Moretta et al., "Different checkpoints in human NK-cell activation", Trends in Immunology, vol. 25, No. 12, Dec. 2004, pp. 670-676, doi: 10.1016/j.it.2004.09.008.
Morikawa et al., "IAPP/amylin deposition, which is correlated with expressions of ASC and IL-1β in β-cells of Langerhans' islets, directly initiates NLRP3 inflammasome activation", International Journal of Immunopathology and Pharmacology, vol. 32, Jul. 17, 2018, 10 pgs., doi: 10.1177/2058738418788749.
Morselli et al., "Autophagy mediates pharmacological lifespan extension by spermidine and resveratrol", Aging, vol. 1, No. 12, Dec. 2009, pp. 961-970, doi: 10.18632/aging.100110.
Neumann et al., "Novel Role of the Antimicrobial Peptide LL-37 in the Protection of Neutrophil Extracellular Traps Against Degradation by Bacterial Nucleases", Jornal of Innate Immunity, vol. 6, No. 6, 2014, pp. 860-868, doi: 10.1159/000363699.
Neumann et al., "The antimicrobial peptide LL-37 facilitates the formation of neutrophil extracellular traps", Biochemical Journal, vol. 464, No. 1, Oct. 23, 2014, pp. 3-11, doi: 10.1042/BJ20140778.
Nixon et al., "Extensive Involvement of Autophagy in Alzheimer Disease: An immuno-Electron Microscopy Study", Journal of Neuropathology & Experimental Neurology, vol. 64, No. 2, Feb. 1, 2005, pp. 113-122, doi: 10.1093/jnen/64.2.113.
Olatunbosun, "Insulin Resistance", Medscape, Jul. 5, 2018, retrieved from: https://emedicine.medscape.com/article/122501-print, 21 pgs.
O'Nuallain et al., "Seeding Specificity in Amyloid Growth Induced by Heterologous Fibrils", Journal of Biological Chemistry, vol. 279, No. 17, Apr. 23, 2004, pp. 17490-17499, doi: 10.1074/jbc.M311300200.
Ordonez et al., "Fungicidal Mechanisms of Cathelicidins LL-37 and CATH-2 Revealed by Live-Cell Imaging", Antimicrobial Agents Chemotherapy, vol. 58, No. 4, Apr. 2014, pp. 2240-2248, doi: 10.1128/AAC.01670-13.

(56) References Cited

OTHER PUBLICATIONS

Oren et al., "Structure and organization of the human antimicrobial peptide LL-37 in phospholipid membranes: relevance to the molecular basis for its non- cell-selective activity", Biochemical Journal, vol. 341, No. 3, 1999, pp. 501-513, doi: 10.1042/0264-6021:3410501.
Orvedahl et al., "Autophagy and viral neurovirulence", Cellular Microbiology, vol. 10, No. 9, 2008, pp. 1747-1756, doi: 10.1111/j.1462-5822.2008.01175.x.
Ottosson et al., "Potent Inducers of Endogenous Antimicrobial Peptides for Host Directed Therapy of Infections", Scientific Reports, vol. 6, Article 36692, Nov. 9, 2016, 11 pgs., doi: 10.1038/srep36692.
Park et al., "Resveratrol Stimulates Sphingosine-1-Phosphate Signaling of Cathelicidin Production", Journal of Investigative Dermatology, vol. 133, No. 8, Aug. 2013, pp. 1942-1949, doi: 10.1038/jid.2013.133.
Park et al., "The dietary ingredient, genistein, stimulates cathelicidin antimicrobial peptide expression through a novel S1P-dependent mechanism", The Journal of Nutritional Biochemistry, vol. 25, No. 7, Jul. 2014, pp. 734-740, doi: 10.1016/j.jnutbio.2014.03.005.
Pearson et al., "Physiological roles for amyloid ß peptides", The Journal of Physiology, vol. 575, No. 1, Aug. 2006, pp. 5-10, doi: 10.1113/jphysiol.2006.111203.
Pena-Quintana et al., "Profile of sodium phenylbutyrate granules for the treatment of urea-cycle disorders: patient perspectives", Patient Preference and Adherence, vol. 2107, No. 11, 2017, pp. 1489-1496, doi: 10.2147/PPA.S136754.

* cited by examiner (A)

$[^{125}I]$IPBF (B)

IPBF (C)

PQ-6

FPYBF-1

(D)

AV-45

(E)

IMPY (F)

| | |
|---|---|
| **IAPP** | KC-NTATCATQRLANFLVHSSNNFGAILSSTNVGSNTY |
| **LL-37** | LLGDFFRKSKEKIGKEFKRIVQRIKDFLRNL-VPRTES |
| **LL-37(1-14)** | LLGDFFRKSKEKIG |
| **LL-37(15-37)** | KEFKRIVQRIKDFLRNLVPRTES |
| **scrLL-37** | GLKLRFEFSKIKGEFLKTPEVRFRDIKLKDNRISVQR |

FIG. 25

SEQUENCE LISTING

```
<160> NUMBER OF SEQ ID NOS: 35

<210> SEQ ID NO 1
<211> LENGTH: 37
<212> TYPE: PRT
<213> ORGANISM: homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35


<210> SEQ ID NO 2
<211> LENGTH: 37
<212> TYPE: PRT
<213> ORGANISM: homo sapiens

<400> SEQUENCE: 2

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35


<210> SEQ ID NO 3
<211> LENGTH: 14
<212> TYPE: PRT
<213> ORGANISM: Homo sapiens

<400> SEQUENCE: 3

Leu Leu Gly Asp Phe Phe Arg Lys Ser Lys Glu Lys Ile Gly
1               5                   10


<210> SEQ ID NO 4
<211> LENGTH: 23
<212> TYPE: PRT
<213> ORGANISM: Homo sapiens

<400> SEQUENCE: 4

Lys Glu Phe Lys Arg Ile Val Gln Arg Ile Lys Asp Phe Leu Arg Asn
1               5                   10                  15

Leu Val Pro Arg Thr Glu Ser
            20


<210> SEQ ID NO 5
<211> LENGTH: 37
<212> TYPE: PRT
<213> ORGANISM: Homo sapiens

<400> SEQUENCE: 5
```

-continued

```
Gly Leu Lys Leu Arg Phe Glu Phe Ser Lys Ile Lys Gly Glu Phe Leu
1               5                   10                  15

Lys Thr Pro Glu Val Arg Phe Arg Asp Ile Lys Leu Lys Asp Asn Arg
            20                  25                  30

Ile Ser Val Gln Arg
        35


<210> SEQ ID NO 6
<211> LENGTH: 15
<212> TYPE: PRT
<213> ORGANISM: Homo sapiens

<400> SEQUENCE: 6

Leu Leu Gly Asp Phe Phe Arg Lys Ser Lys Glu Lys Ile Gly Lys
1               5                   10                  15


<210> SEQ ID NO 7
<211> LENGTH: 17
<212> TYPE: PRT
<213> ORGANISM: Homo sapiens

<400> SEQUENCE: 7

Lys Arg Ile Val Gln Arg Ile Lys Asp Phe Leu Arg Asn Leu Val Pro
1               5                   10                  15

Arg


<210> SEQ ID NO 8
<211> LENGTH: 10
<212> TYPE: PRT
<213> ORGANISM: Homo sapiens

<400> SEQUENCE: 8

Leu Leu Gly Asp Phe Phe Arg Lys Ser Lys
1               5                   10


<210> SEQ ID NO 9
<211> LENGTH: 10
<212> TYPE: PRT
<213> ORGANISM: Homo sapiens

<400> SEQUENCE: 9

Leu Gly Asp Phe Phe Arg Lys Ser Lys Glu
1               5                   10


<210> SEQ ID NO 10
<211> LENGTH: 10
<212> TYPE: PRT
<213> ORGANISM: Homo sapiens

<400> SEQUENCE: 10

Gly Asp Phe Phe Arg Lys Ser Lys Glu Lys
1               5                   10


<210> SEQ ID NO 11
<211> LENGTH: 10
<212> TYPE: PRT
<213> ORGANISM: Homo sapiens

<400> SEQUENCE: 11

Asp Phe Phe Arg Lys Ser Lys Glu Lys Ile
1               5                   10


<210> SEQ ID NO 12
```

<211> LENGTH: 10
<212> TYPE: PRT
<213> ORGANISM: Homo sapiens

<400> SEQUENCE: 12

Phe Phe Arg Lys Ser Lys Glu Lys Ile Gly
1 5 10

<210> SEQ ID NO 13
<211> LENGTH: 10
<212> TYPE: PRT
<213> ORGANISM: Homo sapiens

<400> SEQUENCE: 13

Phe Arg Lys Ser Lys Glu Lys Ile Gly Lys
1 5 10

<210> SEQ ID NO 14
<211> LENGTH: 10
<212> TYPE: PRT
<213> ORGANISM: Homo sapiens

<400> SEQUENCE: 14

Arg Lys Ser Lys Glu Lys Ile Gly Lys Glu
1 5 10

<210> SEQ ID NO 15
<211> LENGTH: 10
<212> TYPE: PRT
<213> ORGANISM: Homo sapiens

<400> SEQUENCE: 15

Lys Ser Lys Glu Lys Ile Gly Lys Glu Phe
1 5 10

<210> SEQ ID NO 16
<211> LENGTH: 10
<212> TYPE: PRT
<213> ORGANISM: Homo sapiens

<400> SEQUENCE: 16

Ser Lys Glu Lys Ile Gly Lys Glu Phe Lys
1 5 10

<210> SEQ ID NO 17
<211> LENGTH: 10
<212> TYPE: PRT
<213> ORGANISM: Homo sapiens

<400> SEQUENCE: 17

Lys Glu Lys Ile Gly Lys Glu Phe Lys Arg
1 5 10

<210> SEQ ID NO 18
<211> LENGTH: 10
<212> TYPE: PRT
<213> ORGANISM: Homo sapiens

<400> SEQUENCE: 18

Glu Lys Ile Gly Lys Glu Phe Lys Arg Ile
1 5 10

<210> SEQ ID NO 19
<211> LENGTH: 10
<212> TYPE: PRT

-continued

<213> ORGANISM: Homo sapiens

<400> SEQUENCE: 19

Lys Ile Gly Lys Glu Phe Lys Arg Ile Val
1 5 10

<210> SEQ ID NO 20
<211> LENGTH: 10
<212> TYPE: PRT
<213> ORGANISM: Homo sapiens

<400> SEQUENCE: 20

Ile Gly Lys Glu Phe Lys Arg Ile Val Gln
1 5 10

<210> SEQ ID NO 21
<211> LENGTH: 10
<212> TYPE: PRT
<213> ORGANISM: Homo sapiens

<400> SEQUENCE: 21

Gly Lys Glu Phe Lys Arg Ile Val Gln Arg
1 5 10

<210> SEQ ID NO 22
<211> LENGTH: 10
<212> TYPE: PRT
<213> ORGANISM: Homo sapiens

<400> SEQUENCE: 22

Lys Glu Phe Lys Arg Ile Val Gln Arg Ile
1 5 10

<210> SEQ ID NO 23
<211> LENGTH: 10
<212> TYPE: PRT
<213> ORGANISM: Homo sapiens

<400> SEQUENCE: 23

Glu Phe Lys Arg Ile Val Gln Arg Ile Lys
1 5 10

<210> SEQ ID NO 24
<211> LENGTH: 10
<212> TYPE: PRT
<213> ORGANISM: Homo sapiens

<400> SEQUENCE: 24

Phe Lys Arg Ile Val Gln Arg Ile Lys Asp
1 5 10

<210> SEQ ID NO 25
<211> LENGTH: 10
<212> TYPE: PRT
<213> ORGANISM: Homo sapiens

<400> SEQUENCE: 25

Lys Arg Ile Val Gln Arg Ile Lys Asp Phe
1 5 10

<210> SEQ ID NO 26
<211> LENGTH: 10
<212> TYPE: PRT
<213> ORGANISM: Homo sapiens -continued

<400> SEQUENCE: 26

Arg Ile Val Gln Arg Ile Lys Asp Phe Leu
1               5                   10

<210> SEQ ID NO 27
<211> LENGTH: 10
<212> TYPE: PRT
<213> ORGANISM: Homo sapiens

<400> SEQUENCE: 27

Ile Val Gln Arg Ile Lys Asp Phe Leu Arg
1               5                   10

<210> SEQ ID NO 28
<211> LENGTH: 10
<212> TYPE: PRT
<213> ORGANISM: Homo sapiens

<400> SEQUENCE: 28

Val Gln Arg Ile Lys Asp Phe Leu Arg Asn
1               5                   10

<210> SEQ ID NO 29
<211> LENGTH: 10
<212> TYPE: PRT
<213> ORGANISM: Homo sapiens

<400> SEQUENCE: 29

Gln Arg Ile Lys Asp Phe Leu Arg Asn Leu
1               5                   10

<210> SEQ ID NO 30
<211> LENGTH: 10
<212> TYPE: PRT
<213> ORGANISM: Homo sapiens

<400> SEQUENCE: 30

Arg Ile Lys Asp Phe Leu Arg Asn Leu Val
1               5                   10

<210> SEQ ID NO 31
<211> LENGTH: 10
<212> TYPE: PRT
<213> ORGANISM: Homo sapiens

<400> SEQUENCE: 31

Ile Lys Asp Phe Leu Arg Asn Leu Val Pro
1               5                   10

<210> SEQ ID NO 32
<211> LENGTH: 10
<212> TYPE: PRT
<213> ORGANISM: Homo sapiens

<400> SEQUENCE: 32

Lys Asp Phe Leu Arg Asn Leu Val Pro Arg
1               5                   10

<210> SEQ ID NO 33
<211> LENGTH: 10
<212> TYPE: PRT
<213> ORGANISM: Homo sapiens

<400> SEQUENCE: 33

-continued

```
Asp Phe Leu Arg Asn Leu Val Pro Arg Thr
1               5                   10


<210> SEQ ID NO 34
<211> LENGTH: 10
<212> TYPE: PRT
<213> ORGANISM: Homo sapiens

<400> SEQUENCE: 34

Phe Leu Arg Asn Leu Val Pro Arg Thr Glu
1               5                   10


<210> SEQ ID NO 35
<211> LENGTH: 10
<212> TYPE: PRT
<213> ORGANISM: Homo sapiens

<400> SEQUENCE: 35

Leu Arg Asn Leu Val Pro Arg Thr Glu Ser
1               5                   10
```

METHOD OF PREVENTING OR TREATING PANCREATIC DYSFUNCTION OR DIABETES BY UPREGULATING HUMAN CATHELICIDIN LL-37 TO INHIBIT ISLET AMYLOID POLYPEPTIDE (IAPP) SELF-ASSEMBLY

CROSS-REFERENCE TO RELATED APPLICATION

This application is a national stage of PCT Patent Application No. PCT/US2021/015531, entitled "Method of Preventing or Treating Pancreatic Dysfunction or Diabetes by Upregulating Human Cathelicidin LL-37 to Inhibit Islet Amyloid Polypeptide (IAPP) Self-Assembly," filed Jan. 28, 2021, which claims the benefit of U.S. provisional application No. 62/967,023, entitled "Method of Preventing or Treating Pancreatic Dysfunction or Diabetes by Upregulating Human Cathelicidin LL-37 to Inhibit Islet Amyloid Polypeptide (IAPP) Self-Assembly," filed Jan. 28, 2020, which are incorporated herein by reference in their entireties.

SEQUENCE LISTING

This application includes material in an electronic Sequence Listing filed concurrently herewith. The material in the electronic Sequence Listing is submitted as an XML (.xml) file entitled "07148.PCT Seq List.xml" created on Jul. 28, 2022, which has a file size of approximately 31 KB. The electronic Sequence Listing is hereby incorporated by reference in its entirety.

FIELD OF THE DISCLOSURE

The present disclosure relates generally to methods for treating diseases of the pancreas (such as type 2 diabetes), and more particularly to methods for modulating cathelicidin gene expression for the treatment of such diseases.

BACKGROUND OF THE DISCLOSURE

Amyloid self-assembly of islet amyloid polypeptide (IAPP) is linked to pancreatic β-cell degeneration and the pathogenesis of type 2 diabetes (T2D). The 37-residue IAPP is secreted from the β-cells together with insulin, and acts in its soluble form as a neuropeptide regulator of glucose homeostasis. However, under conditions of T2D, the intrinsically disordered but highly amyloidogenic IAPP self-assembles into cytotoxic oligomers and amyloid fibrils, which mediate pancreatic inflammation and β-cell degeneration.

SUMMARY OF THE DISCLOSURE

This summary is meant to provide some examples and is not intended to be limiting of the scope of the invention in any way. For example, any feature included in an example of this summary is not required by the claims, unless the claims explicitly recite the features. Various features and steps as described elsewhere in this disclosure may be included in the examples summarized here, and the features and steps described here and elsewhere can be combined in a variety of ways.

In one aspect, a method is provided for preventing or treating type 2 diabetes (T2D). The method comprises (a) diagnosing a subject as suffering from T2D or as being pre-diabetic; (b) monitoring the response to glucose stimulation of at least one islet in the pancreas of the subject by quantitatively imaging glucose metabolism in vivo; (c) establishing a target range for the response to glucose stimulation of the at least one islet; and (d) upregulating cathelicidin gene expression in the subject until the monitored response to glucose stimulation is within the target range.

In another aspect, a method is provided for treating a subject for type 2 diabetes (T2D). The method comprises (a) diagnosing the subject as suffering from T2D; and (b) applying to the subject a pharmaceutically acceptable composition which upregulates cathelicidin gene expression in the subject.

In another aspect, a method is provided for treating a prediabetic subject. The method comprises (a) diagnosing the subject as pre-diabetic or likely to suffer from T2D in the future; and (b) applying to the subject a pharmaceutically acceptable composition which upregulates cathelicidin gene expression in the subject.

In a further aspect, a method is provided for treating islet amyloid polypeptide (IAPP) aggregation and accumulation in the pancreas of a subject. The method comprises (a) detecting the presence of IAPP aggregate accumulation in pancreatic tissues of the subject; and (b) administering to the subject a pharmaceutically acceptable composition which upregulates cathelicidin gene expression in the pancreatic tissues of the subject, and/or systemically.

In another aspect, a method is provided for treating a subject. The method comprises (a) monitoring levels of the cathelicidin peptide LL-37 in the blood of a subject and IAPP amyloid in pancreatic tissues of the subject; and (b) when the condition $L/B<k$ is detected, where L is the level of LL-37 detected, B is the level of IAPP detected, and k is a predetermined threshold value, upregulating cathelicidin gene expression in the subject.

In still another aspect, a method is provided for modulating in vivo IAPP amyloid fibril formation. The method comprises (a) monitoring the level of IAPP amyloid in pancreatic tissues of a subject; and (b) administering to the subject a pharmaceutically active composition which modulates in vivo fibril formation in said pancreatic tissues by inducing the expression of a physiologically effective binding partner for IAPP amyloid.

In yet another aspect, a method is provided for modulating in vivo fibril formation in the pancreatic tissues of a subject. The method comprises (a) co-incubating IAPP amyloid with a physiologically effective binding partner for IAPP amyloid, thereby obtaining co-incubated peptides; (b) creating a pharmaceutical composition from the co-incubated polypeptides; and (c) administering the pharmaceutical composition to a subject.

In still another aspect, a method is provided for inhibiting in vivo IAPP amyloid fibril formation in the pancreatic tissues of a subject in which an equilibrium exists between smaller and larger MW species of IAPP amyloid. The method comprises administering to the subject a pharmaceutical composition which shifts the equilibrium toward the smaller species of IAPP amyloid.

In still another aspect, a method is provided for preventing the formation of IAPP fibrils and plaques in the pancreas by inducing the pancreatic and/or systemic expression of LL-37, which is encoded by the human CAMP gene.

In yet another aspect, a method is provided for treating a subject for type 2 diabetes (T2D). The method comprises (a) diagnosing the subject as suffering from T2D; and (b)

applying to the subject a pharmaceutically acceptable composition comprising a peptidomimetic of LL-37 or a portion thereof.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 1 depicts the fibrillogenesis of IAPP (16.5 μM) alone or with LL-37 (1/1) determined by ThT binding (means (±SD), 3 assays); LL-37 alone is shown for comparison (1 assay).

FIG. 2 is a series of TEM images of solutions from 1a (7 days aged) as indicated (bars, 100 nm); inset in LL-37 image shows LL-37 fibrils (minor population).

FIG. 3 is a graph of cell viability of cultured RIN5fm cells after treatment with IAPP and its mixtures from 1a (7 days aged) determined by MTT reduction (means (±SD), 3 assays (n=3 each)); effects of LL-37 alone are also shown (1 assay, n=3).

FIG. 4 depicts a graph of the IC50 of inhibitory effect of LL-37 on IAPP cytotoxicity determined by titration of IAPP (100 nM; red symbol) with LL-37 and MTT reduction (means (±SD), 3 titration assays (n=3 each)).

FIG. 5 is a graph of the fibrillogenesis of IAPP (16.5 μM) alone or with LL-37 (1/1) following seeding with fIAPP (10%) determined by ThT binding (means (±SD), 3 assays).

FIG. 6 is a graph depicting the determination of the app. Kd by fluorescence spectroscopic titrations. Fluorescence emission spectra of Fluos-IAPP (5 nM) alone or with various amounts of LL-37 (pH 7.4) as indicated. Inset, binding curve (means (±SD), 3 titration assays).

FIG. 7 is a graph and associated photomicrograph depicting the binding of FAM-LL-37 to IAPP monomers and fibrils as determined by DB. IAPP monomers and fibrils (40 μg) were spotted on a nitrocellulose membrane and probed with FAM-LL-37 (200 nM) (results representative of 4 assays).

FIG. 8 is a Far-UV CD spectra of IAPP (5 μM), IAPP-LL-37 (1/1; 5 μM each), and LL-37 (5 μM) (0 h) (pH 7.4); the sum of the spectra of LL-37 and IAPP is also shown.

FIGS. 9-10 are kinetic follow-ups of IAPP misfolding alone (FIG. 9) or with LL-37 via far-UV CD spectroscopy. Spectra of IAPP (FIG. 9) and its 1/1 mixture with LL-37 (FIG. 10) at various time points are shown (conditions as in FIG. 8).

FIG. 11 is a characterization of IAPP-LL-37 hetero-assemblies via cross-linking (pH 7.4), NuPAGE, and WB (IAPP 30 μM; IAPP/LL-37, 1/0.1 or 1/1). A representative gel (n>5) is shown.

FIG. 12 is a graph depicting the fibrillogenesis of IAPP (16.5 μM) alone or following seeding with 10% fIAPP or with 10% LL-37-treated fIAPP determined by ThT binding (means (±SD), 3 assays).

FIG. 13 is a series of TEM images of solutions from 3a: fIAPP seeds, LL-37-treated fIAPP seeds, and IAPP seeded with fIAPP (10%) (red dot) or LL-37-treated fIAPP (10%) (blue dot) (both at 6 h); bars, 100 nm.

FIG. 14 is a graph depicting the fibrillogenesis of IAPP (16.5 μM) alone or in the presence of LL-37(1-14) or LL-37(15-37) (1/1) as determined by ThT binding (means (±SD), 3 assays).

FIG. 15 is a graph depicting the β-cell-damaging effects of solutions from 4a (24 h aged) determined by MTT reduction (RIN5fm cells) (means (±SD), 3 assays (n=3 each)).

FIG. 16 is an identification of LL-37 regions that bind IAPP using peptide microarrays. Glass slides with decamers consisting of overlapping LL-37 sequences (bold) were incubated with Fluos-IAPP (1 μM); visualization by fluorescence. Identified IAPP binding clusters in dashed blue line frames; LL-37 "binding cores", red letters (results representative from 4 assays).

FIG. 19 depicts fibrillogenesis of IAPP (16.5 μM) alone or with scrLL-37 (IAPP/scrLL-37, 1/10) determined by the ThT binding assay (means (±SD), 3 assays).

FIG. 20 depicts the effects on IAPP cytotoxicity: Solutions from S2a (7 days aged) were added to RIN5fm cells and cell damage was assessed by MTT reduction (means (±SD), 3 assays (n=3 each)).

FIG. 21 is a series of TEM images of solutions (7 days aged) from S2a of IAPP alone and its mixture with scrLL-37; bars, 100 nm). In the inset of the TEM image of the mixture, amorphous aggregates, found to be in addition to the fibrils a major aggregate population and most likely corresponding to scrLL-37 (10-fold excess), are shown.

FIG. 22 depicts the effects of scrLL-37 on IAPP conformation studied by far-UV CD spectroscopy: CD spectra of IAPP (5 μM), the mixture of IAPP with scrLL-37 (1/1; 5 μM each), and scrLL-37 (5 μM) (pH 7.4) are shown; for comparison, the sum of the spectra of scrLL-37 and IAPP is also shown.

FIG. 25 depicts the primary structures of IAPP, LL-37, scrambled LL-37 (scrLL-37), and LL-37 segments synthesized and studied (IAPP has a C-terminal amide; LL-37 and related peptides have a C-terminal COOH). IAPP and LL-37 sequence alignment was performed by LALIGN.

DETAILED DESCRIPTION

Figure 1:
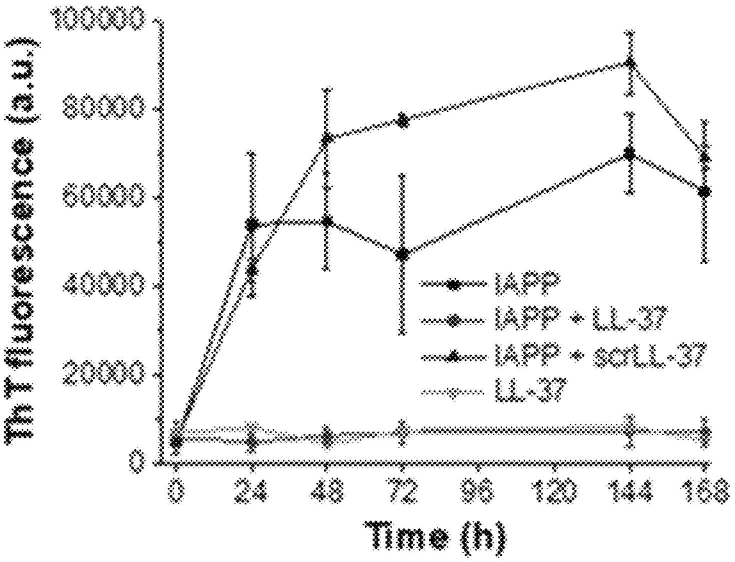
FIGS. 1-5 illustrate the effects of LL-37 on IAPP amyloid self-assembly and cell-damaging effects. Thus.

Turning to the data and figures, when taken together along with the instant disclosure provide, according to many embodiments, methods for treating type 2 diabetes (T2D). Many such embodiments include monitoring the response to glucose stimulation of at least one islet in the pancreas, establishing a target range for the response to glucose stimulation of the at least one islet; and upregulating cathelicidin gene expression in the subject until the monitored response to glucose stimulation is within the target range. Various embodiments are also directed to methods for treating a subject. Many such embodiments include monitoring levels of the cathelicidin peptide LL-37 in the blood of a subject and IAPP amyloid in pancreatic tissues of the subject. Still many embodiments are directed to methods for treating a subject for type 2 diabetes (T2D) including applying to the subject a pharmaceutically acceptable composition comprising a peptidomimetic of LL-37 or a portion thereof.

Type 2 diabetes is characterized by insufficient levels of insulin secretion from pancreatic islet 0-cells to compensate for insulin resistance. Whether a patient with insulin resistance progresses to overt diabetes depends on islet β-cell dysfunction. In order to track the progression of the disease and to understand how various risk factors (such as, for example, obesity) affect proper islet function, it is necessary to have a technique for assessing islet function in vivo. To date, blood insulin measurements are frequently used for this purpose, but such measurements are typically insensitive to small changes, and may be affected by other physiological activities.

Embodiments according to the current disclosure establish that the foregoing issues may be overcome through the use of an imaging platform that combines intrinsic autofluorescence with multiphoton excitation microscopy. This platform provides a noninvasive means for obtaining high-resolution images which may be utilized to quantitatively image real-time glucose metabolism from single islets in vivo, while also offering the advantages of greater imaging depths (and, in some applications, reduced photobleaching and reduced photodamage). Consequently, this technique provides the ability to repeatedly measure an islet's response to glucose stimulation in real time, while also providing the ability to simultaneously monitor islet function, proliferation, vasculature and macrophage infiltration in vivo from a single set of images.

Sun et al. (Sun J, Furio L, Mecheri R, van der Does A M, Lundeberg E, Saveanu L, Chen Y, van Endert P, Agerberth B, Diana J. Pancreatic β-Cells Limit Autoimmune Diabetes via an Immunoregulatory Antimicrobial Peptide Expressed under the Influence of the Gut Microbiota. Immunity. 2015 Aug. 18; 43(2):304-17. doi: 10.1016/j.immuni.2015.07.013. Epub 2015 Aug. 4. PMID: 26253786, the disclosure of which is incorporated by reference) found that antimicrobial peptides (AMPs) expressed by epithelial and immune cells are largely described for the defense against invading microorganisms. Recently, their immunomodulatory functions have been highlighted in various contexts. However, the manner by which AMPs expressed by non-immune cells might influence autoimmune responses in peripheral tissues (such as the pancreas) is unknown.

It has been found that insulin-secreting β-cells produce the cathelicidin related antimicrobial peptide (CRAMP) and that this production is defective in non-obese diabetic (NOD) mice. CRAMP administrated to prediabetic NOD mice induced regulatory immune cells in the pancreatic islets, dampening the incidence of autoimmune diabetes. Additional investigation revealed that the production of CRAMP by β-cells was controlled by short-chain fatty acids produced by the gut microbiota. Accordingly, gut microbiota manipulations in NOD mice modulated CRAMP production and inflammation in the pancreatic islets, revealing that the gut microbiota directly shape the pancreatic immune environment and autoimmune diabetes development.

Amyloid self-assembly of islet amyloid polypeptide (IAPP) is linked to pancreatic inflammation, β-cell degeneration, and the pathogenesis of type 2 diabetes (T2D). The multifunctional host defense peptides (HDPs) cathelicidins play crucial roles in inflammation. It has now been found that the antimicrobial and immunomodulatory polypeptide human cathelicidin LL-37 binds IAPP with nanomolar affinity and effectively suppresses its amyloid self-assembly and related pancreatic β-cell damage in vitro. In addition, key LL-37 segments have been identified which mediate its interaction with IAPP. The foregoing suggests a possible protective role for LL-37 in T2D pathogenesis and offers a molecular basis for the design of LL-37-derived peptides combining antimicrobial, immunomodulatory, and T2D-related anti-amyloid functions as promising candidates for multifunctional drugs.

The multifunctional host defense peptides (HDPs) cathelicidins play crucial roles in inflammatory processes. This includes both pro-inflammatory and anti-inflammatory roles. So far, the only known human cathelicidin is LL-37 (FIG. 25). LL-37 is a 37-residue polypeptide which is broadly expressed by a plethora of immune and non-immune cells, including the β-cells of the pancreas. LL-37 plays a crucial role in innate immunity. Its best known functions are its broad-spectrum antimicrobial activity and its potent immunomodulatory effects. Importantly, secretion of the mouse LL-37 orthologue cathelicidin related antimicrobial peptide (CRAMP) by pancreatic β-cells was recently found to suppress pancreatic β-cell inflammation in a mouse model of type 1 diabetes (T1D) by converting inflammatory cells into regulatory ones. In addition, CRAMP/LL-37 treatment promoted insulin and glucagon secretion and enhanced islet function. Thus, a protective role for LL-37 in T1D has been suggested. The multifunctional nature of LL-37 makes it of high biomedical importance, and numerous studies toward the design of LL-37-derived peptides with antimicrobial or immunomodulatory functions have been reported.

Increasing evidence suggests that interactions of amyloidogenic polypeptides with other polypeptides are crucial modulators of amyloid self-assembly. For instance, high affinity interactions of non-fibrillar species of IAPP with insulin or amyloid β peptide (Aβ40(42)) of Alzheimer's disease (AD) have been found to suppress IAPP amyloidogenesis in vitro. In addition, LL-37 was recently shown to interact with Aβ42, resulting in suppression of Aβ42 amyloidogenesis and neuroinflammation in vitro.

The current disclosure establishes that LL-37 also interacts with IAPP. Notably, LL-37 and IAPP share a remarkable (42%) sequence similarity (Scheme 1). The current disclosure further establishes that LL-37 binds with nanomolar affinity to IAPP and effectively suppresses its amyloid self-assembly and related pancreatic β-cell-damage in vitro. In addition, key LL-37 segments are identified which mediate its interaction with IAPP.

TABLE 1 depicts the primary structures of IAPP, LL-37, scrambled LL-37 (scrLL-37), and LL-37 segments synthesized and studied (IAPP, C-terminal amide; LL-37 and related peptides, C-terminal COOH). IAPP and LL-37 sequence alignment was performed by LALIGN.

TABLE 1

Key LL-37 segments mediating its interaction with IAPP

| | Primary Structure | SEQ ID |
|---|---|---|
| IAPP | KC-NTATCATQRLANFLVHSSNNFGAILSSTNVGSNTY | 1 |
| LL-37 | LLGDFFRKSKEKIGKEFKRIVQRIKDFLRNL-VPRTES | 2 |
| LL-37 (1-14) | LLGDFFRKSKEKIG | 3 |
| LL-37 (15-37) | KEFKRIVQRIKDFLRNLVPRTES | 4 |
| scrLL-37 | GLKLRFEFSKIKGEFLKTPEVRFRDIKLKDNRISVQR | 5 |

Figure 2:
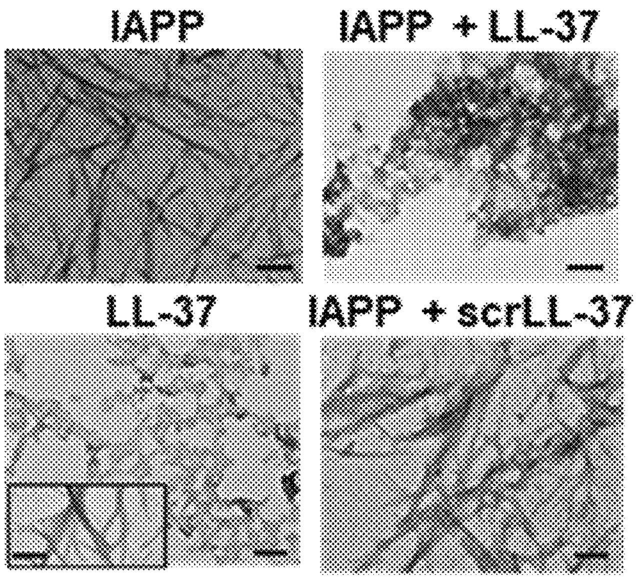
Figure 3:
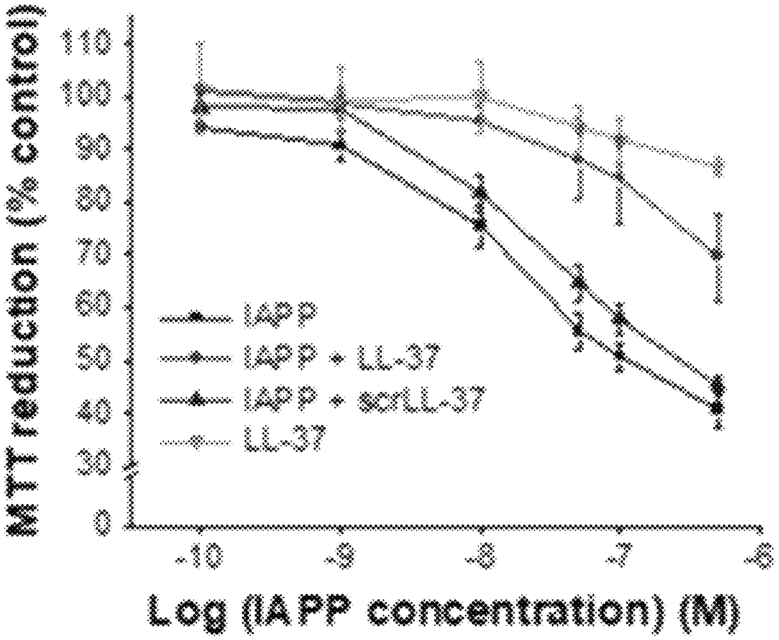
Figure 4:
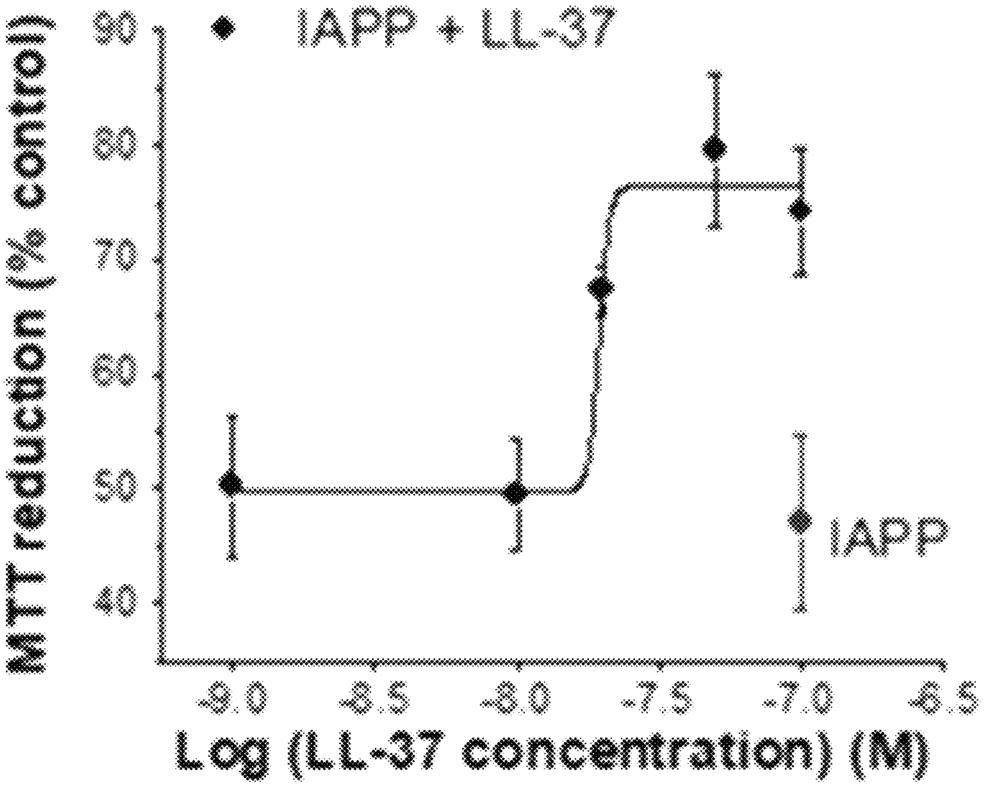
Figure 18:
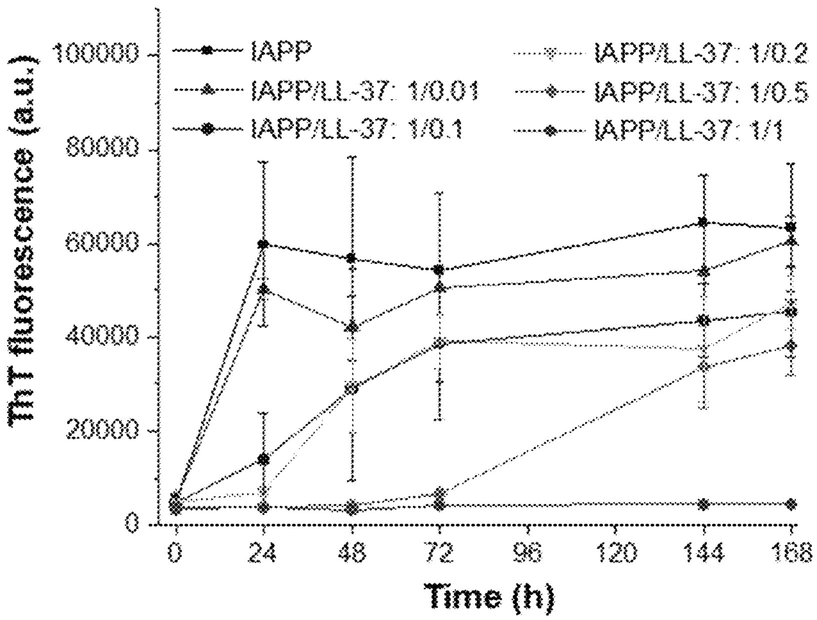
FIG. 18 is a graph showing the dose-dependence of the inhibitory effect of LL-37 on IAPP fibrillogenesis: Fibrillogenesis of IAPP (16.5 μM) alone or with different molar ratios of LL-37 as indicated was determined by the ThT binding assay (means (+SD), 3 assays).

The question was first addressed whether LL-37 might interfere with IAPP amyloidogenesis and formation of cell-damaging assemblies by using the ThT binding assay in combination with TEM and a cell viability assay (FIGS. 1-5). In fact, LL-37 (1/1) effectively suppressed IAPP amyloid self-assembly (FIG. 1). The results of the ThT assay were confirmed by TEM, which revealed amorphous aggregates as major species in aged IAPP-LL-37 mixtures (FIG. 2). Interestingly, a few fibrils were also observed in aged LL-37 alone in addition to amorphous aggregates consistent with previous findings. The dose-dependence of the amyloid inhibitory effect was confirmed by additional studies (FIG. 18). Addition of the above solutions to cultured pancreatic β-cells (RIN5fm) and determination of cell damage via the 3-[4,5-dimethylthiazol-2-yl]-2,5-diphenyltetrazolium bromide (MTT) reduction assay showed that LL-37 effectively suppressed formation of cytotoxic IAPP assemblies as well (FIGS. 3-4). Of note, scrambled LL-37 (scrLL-37) was unable to inhibit up to an at least 10-fold molar excess and LL-37 alone was not cytotoxic (Scheme 1, FIGS. 1-3 & 19).

Figure 5:
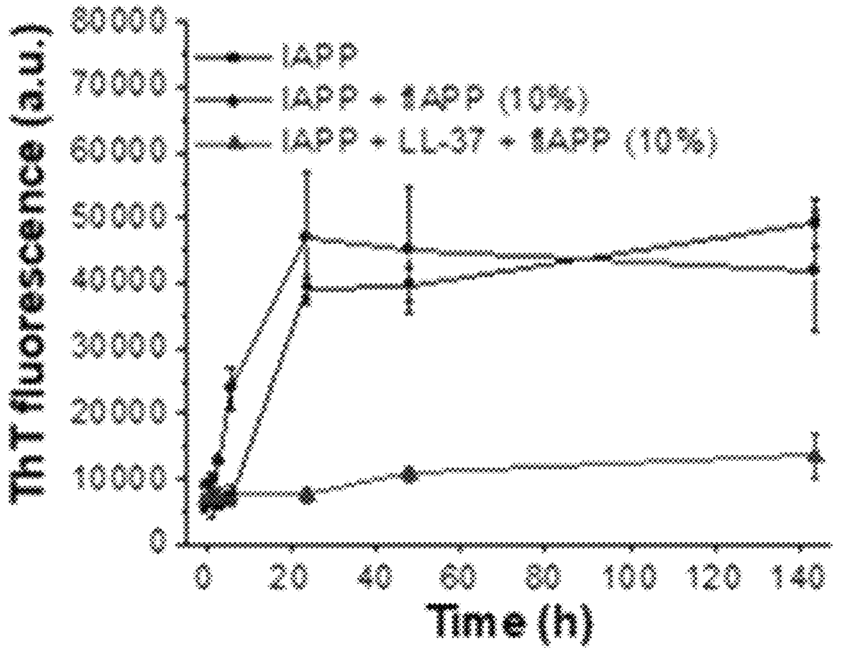

To quantify the inhibitory activity of LL-37, titrations of cytotoxic IAPP with LL-37 were performed and an IC50 of 17 (+1.7) nM was obtained (FIG. 4); thus, LL-37 is a nanomolar inhibitor of IAPP cytotoxic self-assembly. Furthermore, it was investigated whether LL-37 may also interfere with nucleation of IAPP fibrillogenesis by addition of seed amounts of preformed IAPP fibrils (fIAPP). In fact, in the presence of LL-37 (1/1), the seeding effect of fIAPP (10%) was fully suppressed (FIG. 5).

Figure 6:
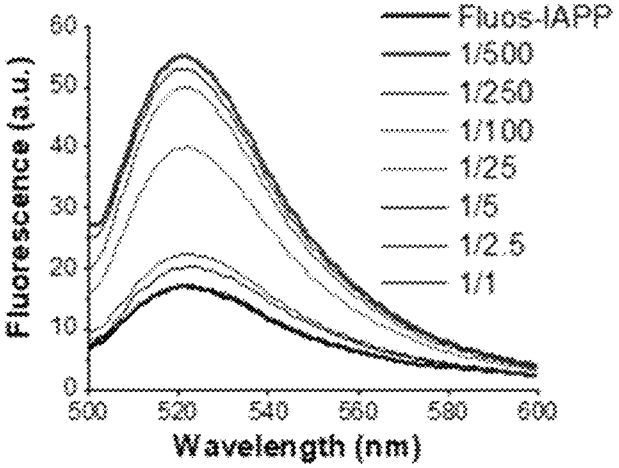
FIGS. 6-11 provide characterization of the LL-37-IAPP interaction.
Figure 7:
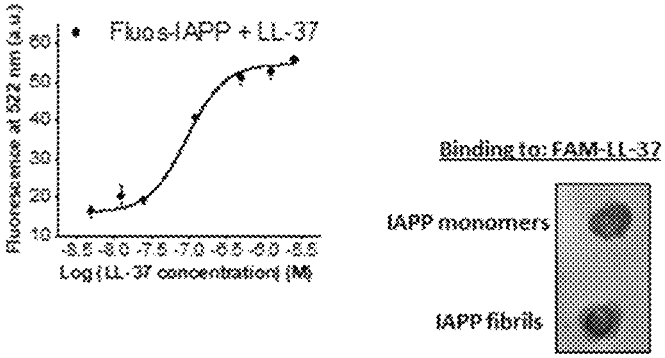

To characterize the LL-37-IAPP interaction, fluorescence spectroscopic titrations, CD spectroscopy, cross-linking, and dot blots (DBs) were performed. First, titration of N-terminal fluorescein labeled IAPP (Fluos-IAPP; 5 nM) with various amounts of LL-37 was performed. Its interaction with 100-fold molar excess of LL-37 resulted in a 322% increase of its fluorescence emission (FIG. 6). The titration yielded an apparent (app.) Kd of 88.1 (+12) nM consistent with a high affinity interaction (FIG. 6). As freshly made solutions of Fluos-IAPP at 5 nM consist mainly of monomers, these results suggested that LL-37 binds monomeric IAPP with nanomolar affinity. To find out whether LL-37 binds IAPP fibrils as well, DBs were performed using N-terminal fluorescein-labeled LL-37 (FAM-LL-37). In fact, FAM-LL-37 bound both IAPP fibrils and monomers (FIG. 7).

Figure 8:
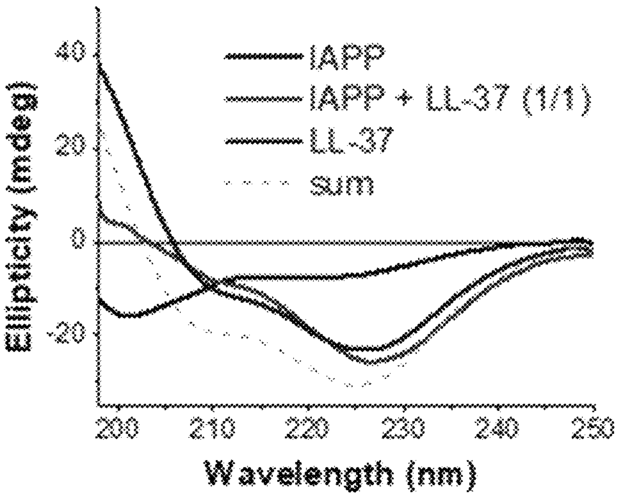
Figure 9:
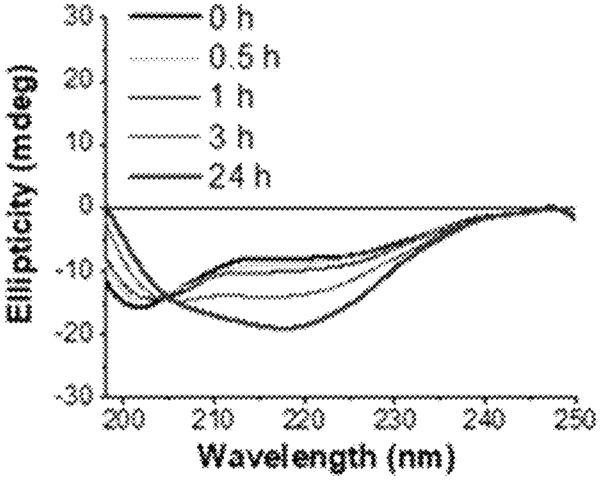
Figure 10:
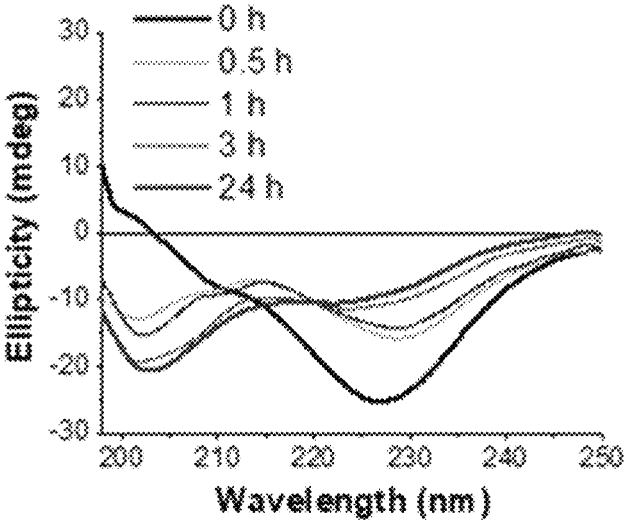
Figure 19:
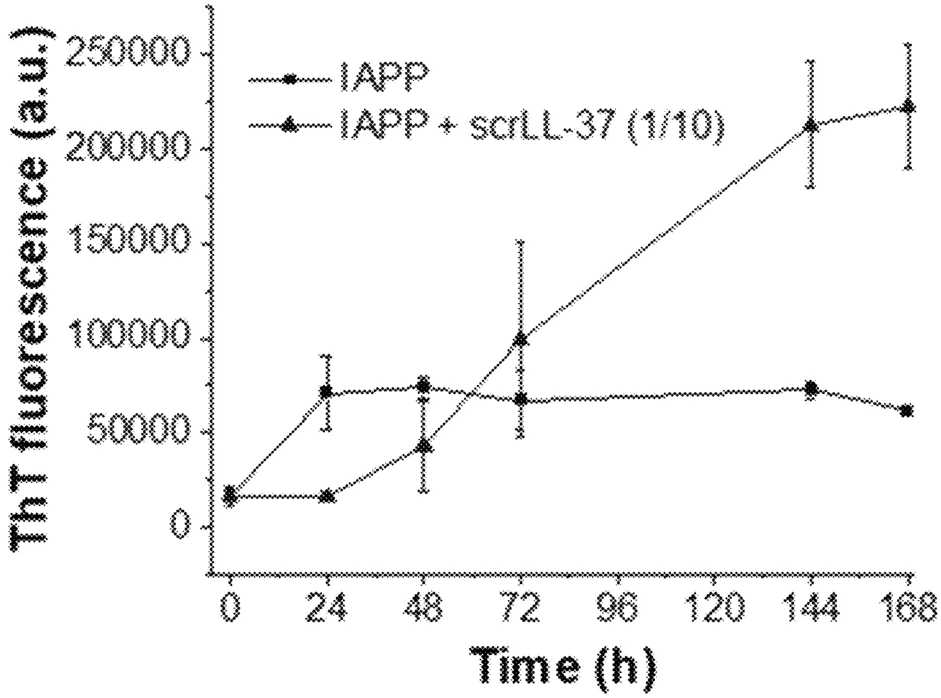
FIGS. 19-22 depict the effects of scrLL-37 on IAPP fibrillogenesis, cell-damaging effects, and conformation.

To determine the effects of LL-37 on IAPP conformation and misfolding, far-UV CD spectra of IAPP, LL-37, and the IAPP-LL-37 mixture (1/1) were measured at various incubation time points (FIGS. 8-10). The spectrum of IAPP (0 h) exhibited a strong minimum at ~200 nm indicative of large amounts of unordered structure (FIG. 8). By contrast, the spectrum of LL-37 exhibited a strong $n \rightarrow \pi^*$minimum at ~227 nm, a smaller one at ~210 nm, and a maximum at ~198 nm. These features were indicative of large amounts of α-helix and/or β-sheet/turn structure. Importantly, the spectrum of the mixture differed from the sum of the spectra, thus confirming the interaction between the two peptides (FIG. 8). In addition, the CD spectra of the mixture and of LL-37 were very similar to each other; α-helical homo- or hetero-oligomers could account for their 227 and 210 nm minima (FIG. 8). In fact, LL-37 has a well-known propensity to self-assemble into α-helical oligomers, while α-helix-mediated homo-dimerization may precede IAPP amyloid self-assembly. Of note, scrLL-37 (1/1) did not affect IAPP conformation (FIG. 19).

The CD spectra of IAPP at various incubation time points indicated a conformational transition into β-sheet-rich assemblies, leading to fibril formation and precipitation (24 h) (FIG. 9). By contrast, the LL-37-IAPP mixture exhibited a strong time-dependent increase of random coil contents and no precipitation occurred (FIG. 10). Thus, the LL-37-IAPP interaction resulted in soluble, partly disordered hetero-assemblies which suppressed IAPP fibrillogenesis.

Figure 11:
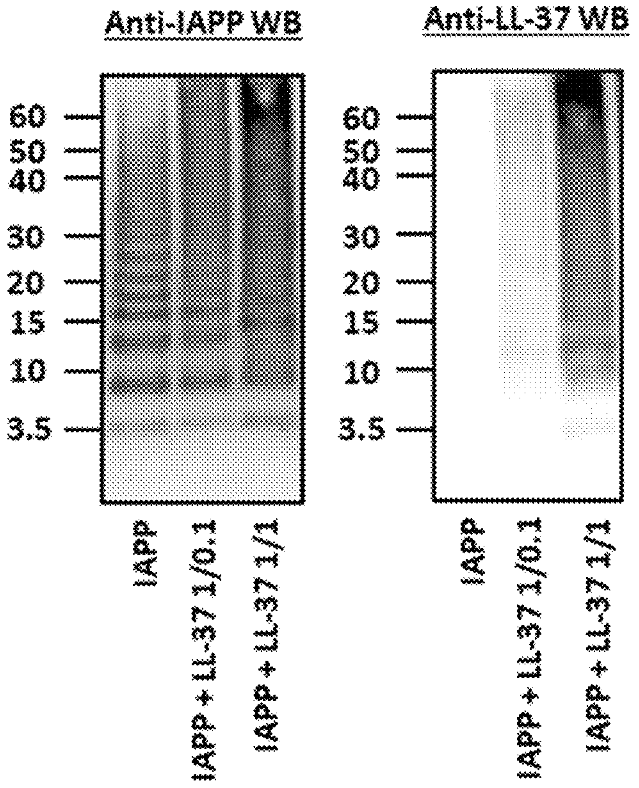
Figure 20:
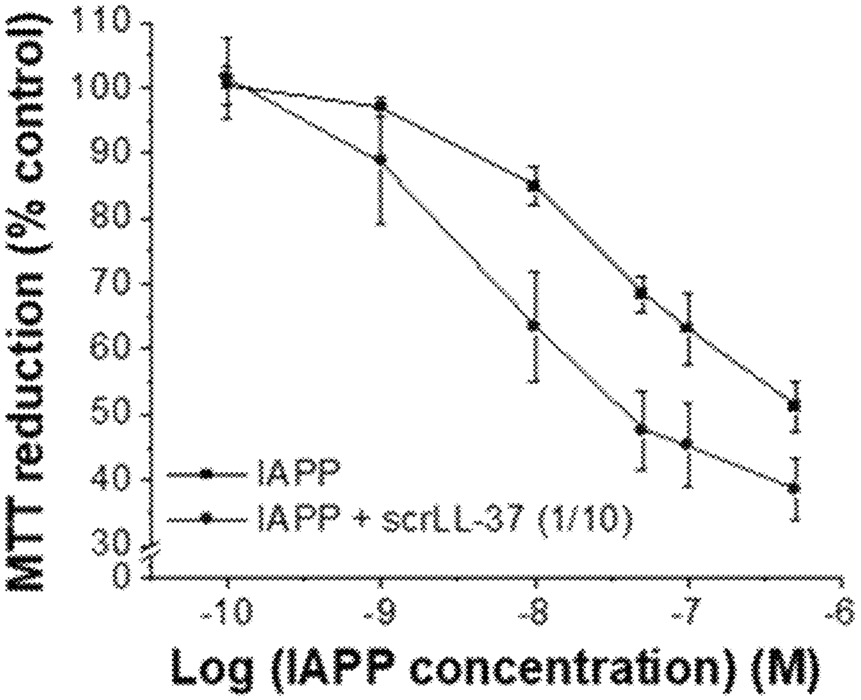

To further characterize the LL-37-IAPP hetero-assemblies, cross-linking studies were performed. LL-37-IAPP hetero-assemblies were cross-linked with glutaraldehyde, separated by NuPAGE, and visualized by Western Blot (WB) analyses with anti-IAPP and anti-LL-37 antibodies. IAPP or LL-37 alone were cross-linked as well. IAPP solutions contained low MW oligomers, mostly di- to hexamers while the smear at the upper part of the gel indicated higher MW aggregates (FIG. 11). A similar pattern was observed in the presence of non-inhibitory amounts (0.1 equivalents) of LL-37. By contrast, in the presence of an inhibitory (equimolar) LL-37 amount a novel prominent band, which was absent in the IAPP alone incubations, was found at ~15 kDa and suggested formation of IAPP-LL-37 hetero-tetramers (FIG. 11, left panel). In addition, a strong reduction of low MW oligomeric IAPP bands likely corresponding to cytotoxic IAPP oligomers was observed (FIG. 11, left panel). WB with anti-LL-37 antibody confirmed the presence of LL-37 in the 15 kDa band of the IAPP-LL-37 mixtures (FIG. 11, right panel). Notably, LL-37 alone contained also a band at ~15 KDa corresponding to LL-37 homo-tetramers (FIG. 20). Together, the cross-linking studies identified LL-37-IAPP hetero-tetramers as major hetero-oligomeric populations and suggested that their formation may underlie the inhibitory effect of LL-37 on IAPP amyloid self-assembly.

Figure 12:
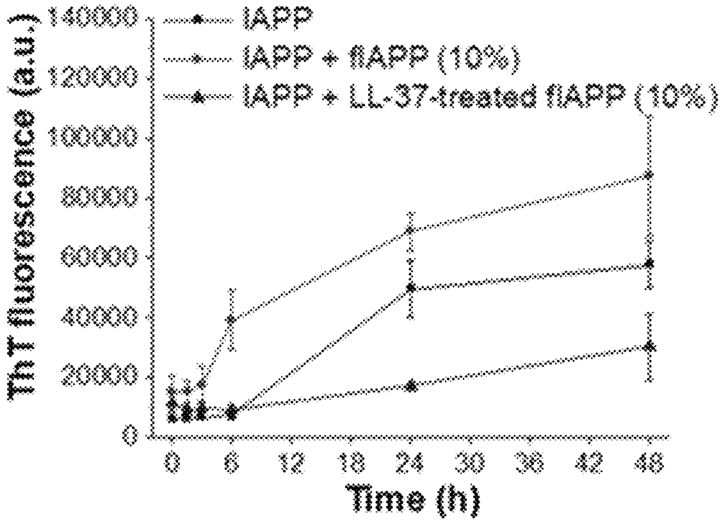
FIGS. 12-13 depict the LL-37 binding to IAPP fibrils (fIAPP) converts them into seeding incompetent assemblies.
Figure 13:
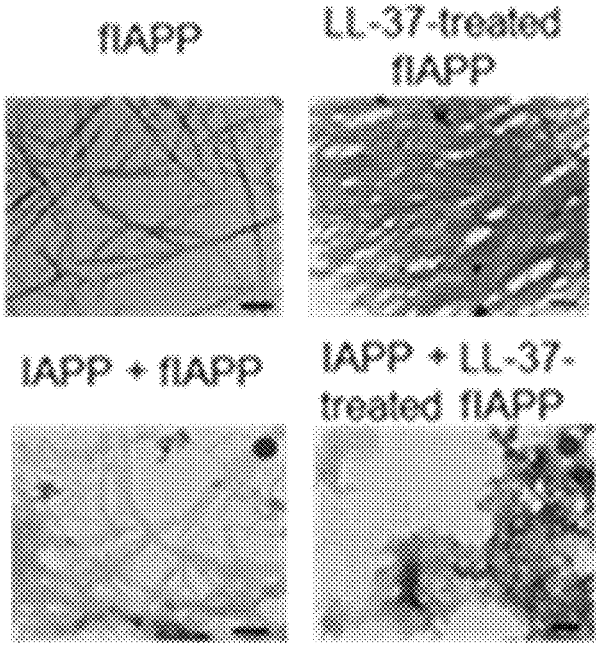

As LL-37 was found to bind to IAPP fibrils (fIAPP) as well, it was investigated whether this interaction might also contribute to its amyloid inhibitor effect. To address this, preformed fIAPP versus LL-37-treated fIAPP (i.e. fIAPP incubated with LL-37 (10-fold) for 24 h) were studied regarding their ability to act as seeds of IAPP fibrillogenesis. In contrast to untreated fIAPP (10%), which strongly accelerated IAPP fibrillogenesis, LL-37-treated fIAPP (10%) were unable to do so (FIGS. 12-13). TEM revealed marked morphological differences between fIAPP and LL-37-treated fIAPP, which stick laterally to each other into large sheet-like assemblies (FIG. 13). Thus, binding of LL-37 to IAPP fibrils converts them into seeding incompetent assemblies providing an additional mechanistic explanation for its potent amyloid inhibitor function.

Figure 14:
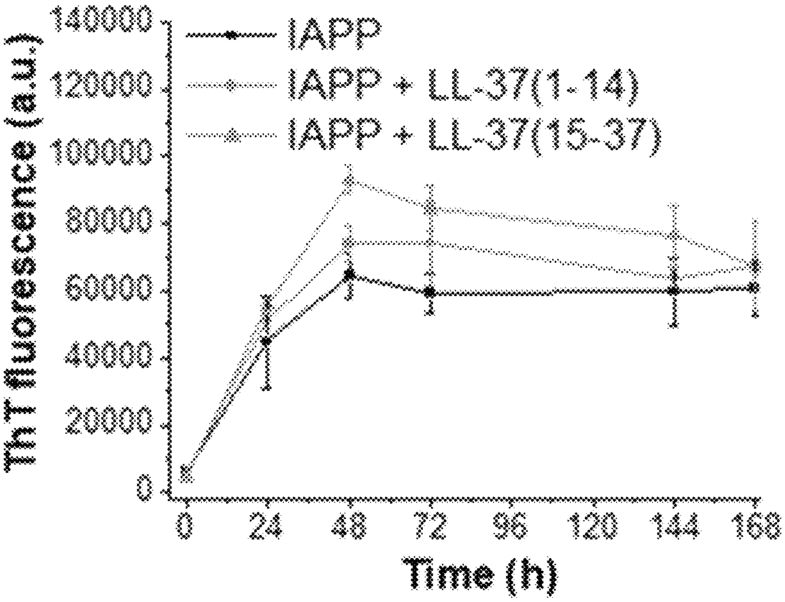
FIGS. 14-16 illustrate the identification of LL-37 regions mediating its interaction with IAPP and its potent amyloid inhibitor function.
Figure 15:
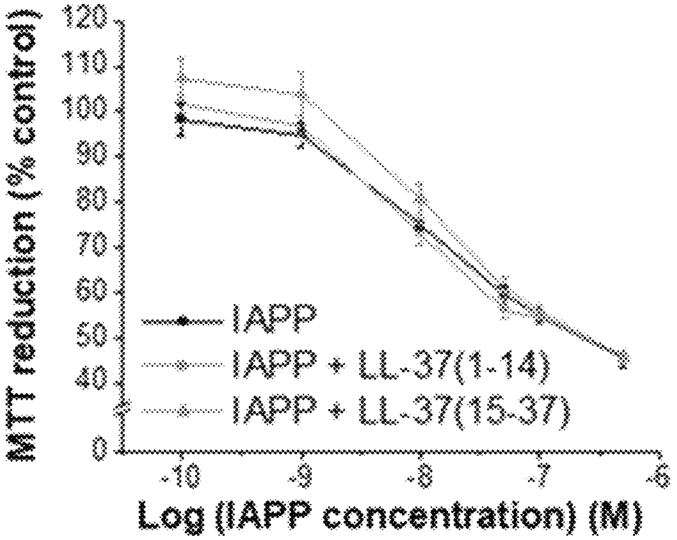
Figure 21:
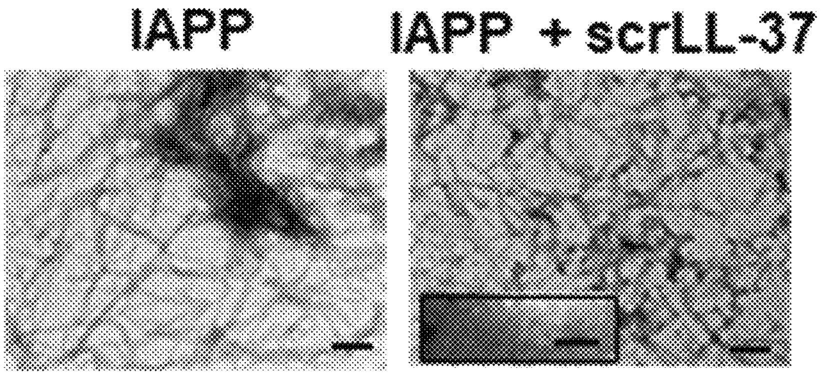
Figure 22:
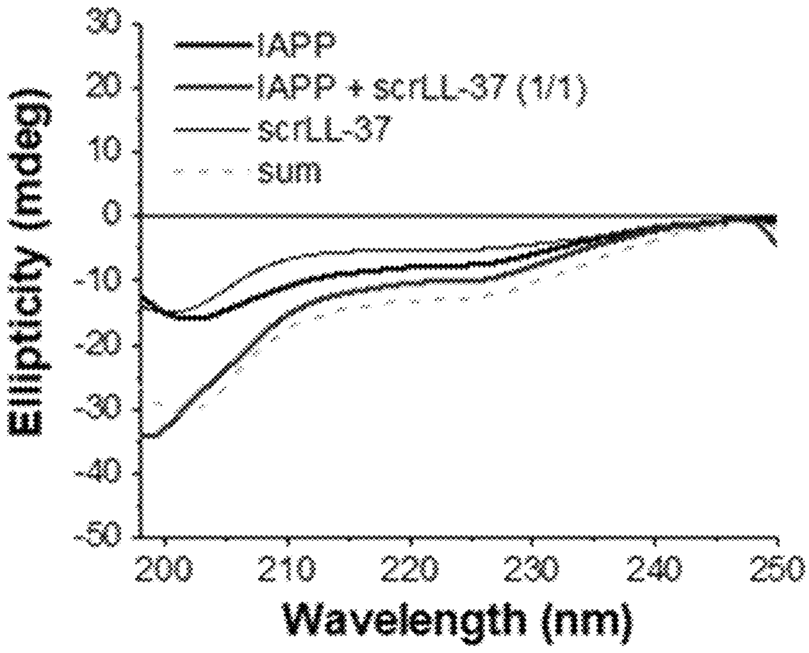
Figure 23:
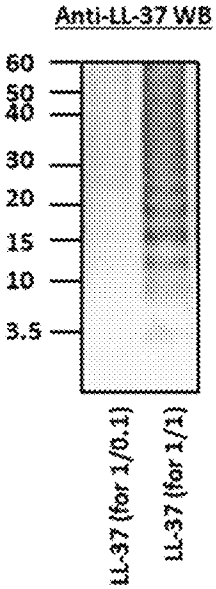
FIG. 23 is a characterization of LL-37 homo-oligomers (including homo-tetramers at ~15 kDa) via cross-linking with glutaraldehyde, NuPAGE, and WB with anti-LL-37 antibody: LL-37 was incubated (30 min) at concentrations of 3 and 30 μM corresponding to IAPP/LL-37 ratios of 1/0.1 or 1/1 alone or in the presence of IAPP (30 μM; gel shown in FIG. **2*f***) (pH 7.4). The blot shown is representative of 3 experiments.

Specific partial LL-37 sequences within its central/C-terminal parts such as LL-37(17(18)-29) or LL-37(13-32) have been found to be sufficient for antibacterial, antiviral, or immunomodulatory activities and are thus being used for drug design. To find out whether the amyloid inhibitor function of LL-37 resides within specific sequence parts as well, it was dissected into the two segments LL-37(1-14) and LL-37(15-37) containing its N- and central/C-terminal helical parts. The peptides were synthesized, and their interactions and effects on IAPP amyloid self-assembly were studied. Importantly, both segments were unable to interfere with IAPP amyloid self-assembly and cell-damaging effects (1/1) (FIGS. 14-15). In addition, fluorescence titrations revealed that LL-37(15-37) bound Fluos-IAPP with high affinity (app. Kd=31.9 (+2.2) nM) as full length LL-37 as well; by contrast, a ~30-fold weaker binding (app. Kd=2.54 (+0.5) μM) was found for LL-37(1-14) (FIG. 21). Thus, while the central/C-terminal LL-37 part likely mediates its high affinity interaction with IAPP, it is not sufficient for amyloid inhibitor function; the concerted action of central/C-terminal and N-terminal parts appears to be required.

Figure 16:
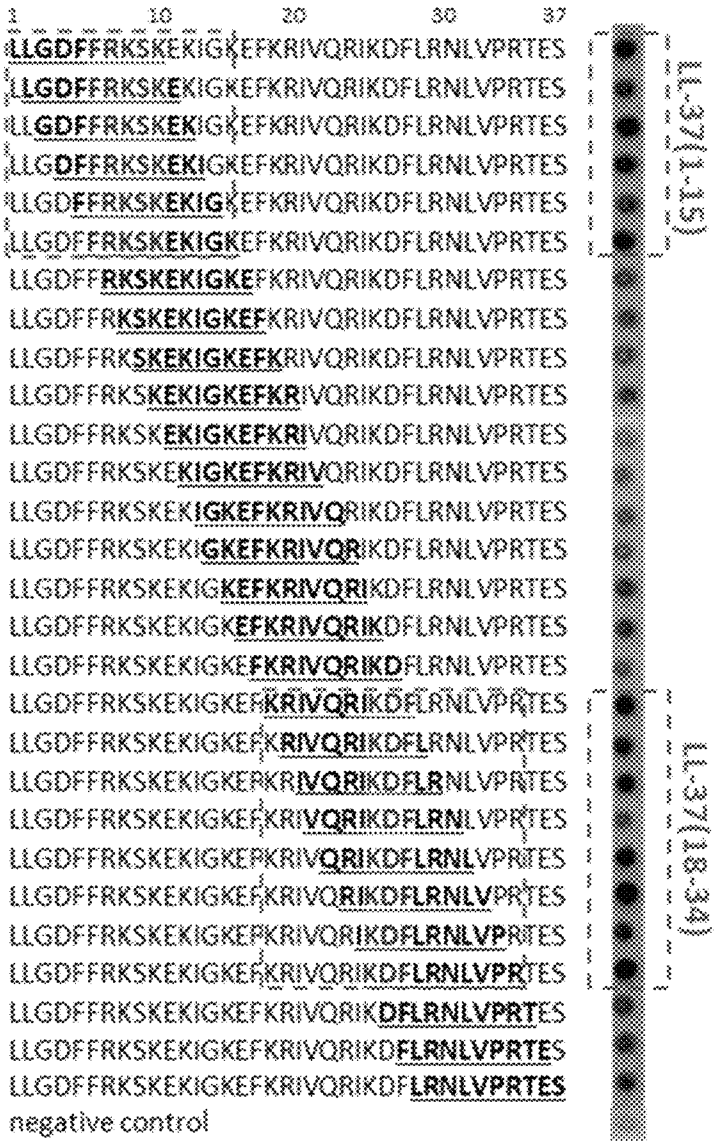

To better characterize the LL-37 regions involved in its interaction with IAPP, peptide arrays of 10-residue LL-37 segments were used covering full length LL-37 and positionally shifted by one residue; peptides were covalently attached on glass slides. Incubation with Fluos-IAPP revealed two clusters of 6-8 consecutive IAPP binding segments: the first one in the N-terminal sequence LL-37 (1-15) and the second one in the C-terminal sequence LL-37(18-34) (FIG. 4*c*). The common sequence parts within each binding cluster (i.e., the "binding cores") were LL-37 (6-10) or FRKSK at the N-terminus, and LL-37(25-27) or KDF within the C-terminal part (FIG. 16). These findings were in line with the LL-37 dissection studies. In addition, they identified the segments mediating its interaction with IAPP.

Figure 17:
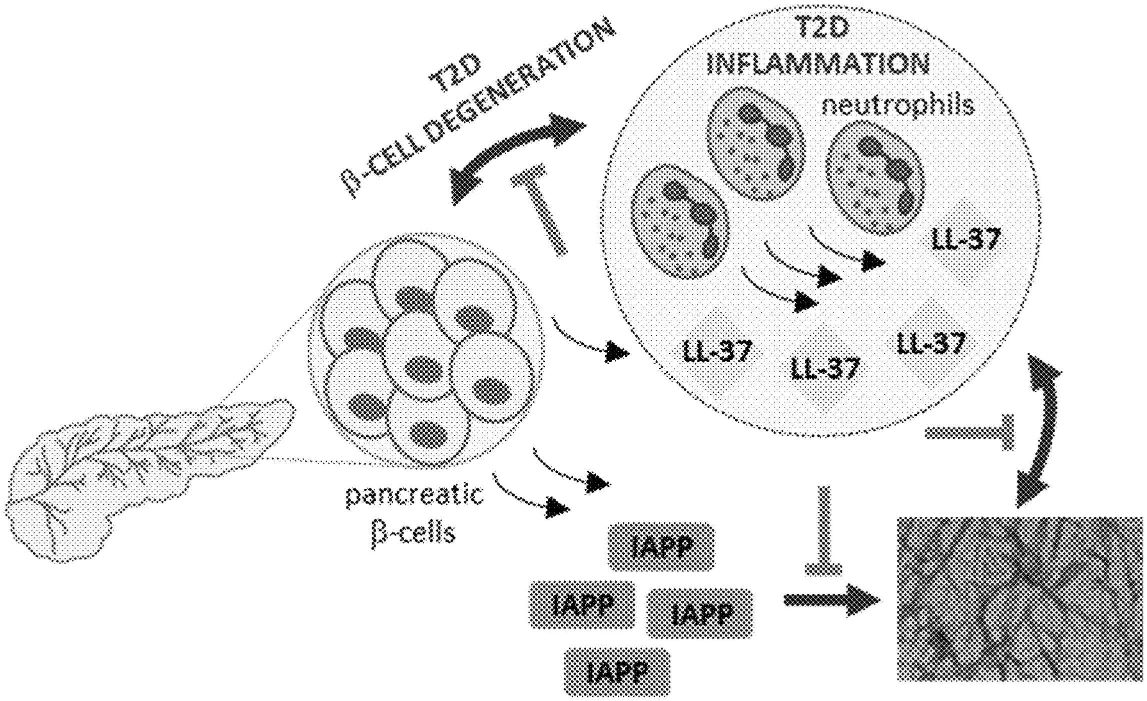
FIG. 17 is an illustration of the suggested protective role of LL-37-IAPP interaction in pancreatic amyloid formation, inflammation, β-cell degeneration, and T2D pathogenenesis.

In summary, a high affinity interaction was identified between LL-37 and IAPP which effectively suppresses IAPP amyloid self-assembly in vitro, and key LL-37 segments mediate this interaction. These results suggest that LL-37 inhibitor function is mediated via its binding (a) to early prefibrillar IAPP species and their sequestration into soluble, non-fibrillar hetero-assemblies, and (b) to IAPP fibrils and their conversion into seeding incompetent assemblies. Together with findings by others, these results support the hypothesis that LL-37, secreted by pancreatic β-cells or infiltrated neutrophils under conditions of pancreatic inflammation, binds IAPP and suppresses its amyloid self-assembly and related β-cell damage, thus slowing down T2D pathogenesis (FIG. 17). Studies on the potential physiological relevance of the LL-37-IAPP interaction are now of high priority.

It will thus be appreciated that a high affinity amyloid suppressing interaction has been uncovered between a major antimicrobial and immunomodulatory polypeptide and the key amyloid polypeptide of T2D. This interaction offers a molecular basis for the design of novel molecules combining antimicrobial, immunomodulatory, and T2D-related anti-amyloid functions as candidates for multifunctional drugs.

Endogenous fluorescent cofactor NAD(P)H is a major autofluorescence signal in the cell. Because NAD(P)+ is nonfluorescent, imaging of NAD(P)H levels has been used to quantify the in situ redox state and mitochondrial function. In pancreatic islets, a method has been established to use NAD(P)H to study glucose-stimulated insulin secretion (GSIS) in vitro.

Quantitative NAD(P)H imaging of the type described herein may be utilized to directly measure glucose metabolism, and to correlate autofluorescence signals with downstream glucose-stimulated events. When glucose enters the pancreatic β-cell, NADH is first generated through glycolysis and the citric acid cycle. This phenomenon results in an increase in the ATP/ADP ratio that eventually culminates in $Ca^{2+}$ influx and insulin secretion. The rise in cytosolic $Ca^{2+}$ levels is followed by an increase in mitochondrial $Ca^{2}$ levels, which activates several dehydrogenases that form NADH in the mitochondria. This interdependence between NAD(P)H and intracellular $Ca^{2+}$ is leveraged in some embodiments of the imaging techniques described herein to measure pancreatic β-cell function. In contrast to other in vivo imaging techniques, which typically permit monitoring of only a single aspect of islet function at a time, this approach may be utilized to simultaneously monitor multiple aspects of glucose metabolism and glucose-stimulated events from a single set of images. Thus, for example, this technique may be utilized to identify, from a single set of images, changes in glucose metabolism, islet proliferation, fibrosis, vasculature and macrophage infiltration. This is preferably accomplished through the use of multiple sources of tissue autofluorescence, which may be acquired simultaneously using multiphoton microscopy (See, e.g., Li G, Wu B, Ward M G, Chong A C, Mukherjee S, Chen S, Hao M. Multifunctional in vivo imaging of pancreatic islets during diabetes development. J Cell Sci. 2016 Jul. 15; 129(14):2865-75. doi: 10.1242/jcs.190843. Epub 2016 Jun. 6. PMID: 27270669; PMCID: PMC4958299, the disclosure of which is incorporated herein by reference).

This technique allows glucose metabolism to be imaged directly, in vivo, and in real-time in individual human islets. The technique may be applied to study human islet function at various stages during the development of diabetes, and may be utilized in conjunction with the methods disclosed herein for inducing CAMP gene expression to assess the efficacy and need for induction. Of course, while this technique is especially suitable for imaging glucose metabolism, it is also to be noted that, because many tissues in the human body share autofluorescence properties, imaging platforms of the type disclosed herein may be readily and suitably adopted to investigate or monitor a wide range of biological systems.

Various autofluorescence signals may be utilized in the devices and methodologies disclosed herein. These signals may be utilized as intrinsic biomarkers to yield detailed molecular information under both physiologic and disease states. Quantification of cellular NAD(P)H may be leveraged to monitor redox state and mitochondrial function. Cytoplasmic and mitochondrial NAD(P)H changes may be measured to resolve the spatiotemporal partitioning of glycolytic and oxidative metabolism. The distinct roles of NADH and NAD(P)H in ATP production and antioxidant defense may be resolved by simultaneously measuring two-photon NAD(P)H and one-photon lipoamide dehydrogenase autofluorescence or by fluorescence lifetime imaging. Modeling of the dynamics of lipid partitioning and fatty acid oxidation may be achieved through suitable monitoring of electron transfer flavoprotein autofluorescence. Finally, quantitative studies based on cellular autofluorescence may be utilized to distinguish between healthy and cancerous cells.

Figure 24:
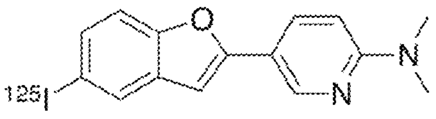
FIG. 24 is a set of β-amyloid imaging probes which may be utilized to image pancreatic islets.
Figure 24:
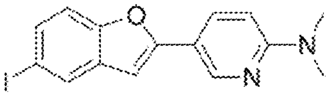
Figure 24:
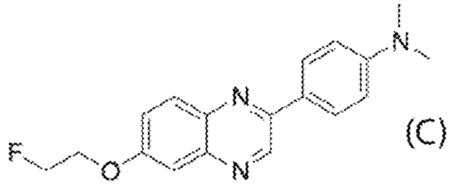
Figure 24:
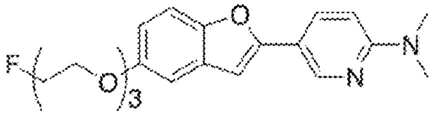
Figure 24:
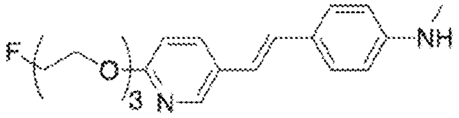
Figure 24:
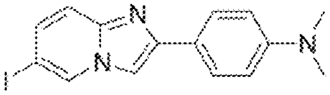

In some embodiments of the systems and methodologies disclosed herein, imaging techniques may also be employed for pancreatic islets which utilize suitable β-Amyloid imaging probes. Such probes may, for example, target amylin or other substances associated with islet amyloid deposits. These probes may be molecules that exhibit high binding affinities for Aβ aggregates to allow Aβ plaques to be visualized in vivo (See, e.g., Yoshimura M, Ono M, Watanabe H, Kimura H, Saji H. Feasibility of amylin imaging in pancreatic islets with β-amyloid imaging probes. Sci Rep. 2014; 4:6155. Published 2014 Aug. 21. doi: 10.1038/srep06155, the disclosure of which is incorporated herein by reference). Some particular, nonlimiting examples of probes which may be utilized for this purpose include the probes set forth in FIG. 24.

In some embodiments, positron emission tomography (PET) may be utilized in combination with amyloid imaging probes for PET detection of islet amyloid deposits. One example of such a probe is the $^{18}$F-labelled radiopharmaceutical florbetapir, which has been used elsewhere in the detection of Aβ-derived amyloid deposits in the brain for diagnosis of Alzheimer's disease. Here, it is to be noted that brain and islet amyloid deposits, though distinct, also share some structural similarities (see, e.g., Kayed R, Head E, Thompson J L, et al. (2003) Common structure of soluble amyloid oligomers implies common mechanism of pathogenesis. Science. 300(5618):486-9, the disclosure of which is incorporated herein by reference).

Various other imaging techniques and platforms may also be utilized in the systems and methodologies described herein. These include, without limitation, positron emission tomography (PET) and magnetic resonance imaging (MRI). In some embodiments, imaging techniques which utilize perfusion with $Ca^{2+}$ probes or viral transduction of fluorescent reporters may also be utilized.

Various pharmaceutical compositions may be utilized in accordance with the teachings herein to upregulate cathelicidin gene expression in the subject, to induce the expression of a physiologically effective binding partner for IAPP amyloid, to inhibit in vivo IAPP amyloid fibril formation in the pancreatic tissues of a subject, to shift an equilibrium which exists between smaller and larger MW species of IAPP amyloid toward the smaller species of IAPP oligomers and fibrils, or to reduce the level of IAPP in the tissues below the threshold amount by inducing LL-37 production in the pancreatic tissues. In some embodiments, these pharmaceutically acceptable compositions preferably include a mixture of at least four more preferably at least five, and most preferably at least six materials (preferably active materials) selected from the group consisting of phenylbutyrate, bexarotene, curcumin, resveratrol, retinol, cholecalciferol, fatty acids, and pharmaceutically acceptable salts thereof. In other embodiments, the pharmaceutically acceptable compositions disclosed herein preferably include a mixture of at least four more preferably at least five, and most preferably at least six materials (preferably active materials) selected from the group consisting of phenylbutyrate, bexarotene, curcumin, resveratrol, retinol, cholecalciferol, docosahexaenoic acid, caprylic acid, capric acid, lauric acid, and pharmaceutically acceptable salts thereof. In still other embodiments, the pharmaceutical composition may comprise the Bacille Calmette-Guerin (BCG) vaccine.

These pharmaceutical compositions may utilize one or more active ingredients (and will preferably utilize multiple active ingredients, as noted above) which may be dissolved, suspended or disposed in various media. Such media may include, for example, various liquid, solid or multistate media such as, for example, emulsions, gels or creams. Such media may include liquid media, which may be hydrophobic or may comprise one or more triglycerides or oils. Such media may include, but is not limited to, vegetable oils, fish oils, animal fats, hydrogenated vegetable oils, partially hydrogenated vegetable oils, synthetic triglycerides, modified triglycerides, fractionated triglycerides, and mixtures thereof. Triglycerides used in these pharmaceutical compositions may include those selected from the group consisting of almond oil; babassu oil; borage oil; blackcurrant seed oil; black seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoleic glycerides; caprylic/capric glycerides; modified triglycerides; fractionated triglycerides; and mixtures thereof. The use of coconut oil or MCT (medium chain triglyceride) oil is especially preferred.

Various fatty acids may be utilized in the pharmaceutical compositions disclosed herein. These include, without limitation, both long and short chain fatty acids. Examples of such fatty acids include, but are not limited to, docosahexaenoic acid, caprylic acid, capric acid, lauric acid, butyric acid, and pharmaceutically acceptable salts thereof.

The pharmaceutical compositions disclosed herein may be applied in various manners. Thus, for example, these compositions may be applied as oral, transdermal, transmucosal, intravenous or injected treatments, or via cell-based drug delivery systems. Moreover, these compositions may be applied in a single dose, multi-dose or controlled release fashion.

The pharmaceutical compositions disclosed herein may be manufactured as tablets, liquids, gels, foams, ointments or powders. In some embodiments, these compositions may be applied as microparticles or nanoparticles.

Various counterions may be utilized in forming pharmaceutically acceptable salts of the materials disclosed herein. One skilled in the art will appreciate that the specific choice of counterion may be dictated by various considerations. However, the use of sodium and hydrochloride salts may be preferred in some applications.

In some embodiments of the systems and methodologies disclosed herein, rather than upregulating cathelicidin gene expression in the subject, peptoid mimics or peptidomimetics of LL-37 or its fragments may be utilized or administered to the subject for similar purposes. These may include modified peptides, structural mimetics (including peptidic foldamers), and mechanistic mimetics.

In some embodiments, a plurality of mimetics may be utilized, which may or may not be connected by a linker moiety. For example, in one such embodiment, two mimetics (peptidomimetics) of LL-37 binding regions may be connected by a flexible peptoid linker such as, for example, an oligo-N-methoxyethylglycine or oligo-Nmeg. However, various other linker moieties may also be utilized including, but not limited to, peptides, PEG, peptoids, 7-aminoheptanoic acid (AHA), alkyl linkers, and linkers containing disulfide or triazole-moieties. Preferably, the peptidomimetics include a first mimetic of the N-terminal sequence LL-37(1-15) of LL-37, and a second mimetic of the C-terminal sequence LL-37(18-34) of LL-37. More preferably, the peptidomimetics include a first mimetic of the LL-37(6-10) or FRKSK of LL-37 at the N-terminus, and a second mimetic of the LL-37(25-27) or KDF region within the C-terminal part of LL-37.

EXEMPLARY EMBODIMENTS

The following embodiments are provided to further disclose and elucidate the current disclosure. These embodiments are of an exemplary nature and are not meant to limit the scope of the disclosure.

Peptides and Peptide Synthesis

IAPP was synthesized using Fmoc-solid phase synthesis strategy on Rink resin, oxidized with air and purified with reverse phase (RP) HPLC as previously described. IAPP stock solutions were made by dissolving the peptide in 1,1,3,3,3,3-hexafluoro-2-isopropanol (HFIP) (at 4° C.) and filtering the solution as described; IAPP concentration was determined by UV spectroscopy. $N^h$-amino-terminal fluorescein labeled IAPP (Fluos-IAPP) was synthesized, purified (MALDI-TOF MS: found MH+, 4261.2; calculated 4262.2), and handled as previously described. LL-37 was purchased from BACHEM and from AnaSpec; its stock solutions were made by dissolving it in HFIP (at 4° C.); its concentration was determined by its weight and the BCA assay. Scrambled LL-37 (scrLL-37) and N-amino-terminal fluorescein labeled LL-37 (FAM-LL-37) were purchased from Anaspec; of note, a 6-aminohexanoic acid spacer was included between the fluorescein (FAM) moiety and the N-terminus of LL-37 in FAM-LL-37. Synthetic glucagon (control for dot blot assays) was from BACHEM. The LL-37 partial segments LL-37(1-14) and LL-37(15-37) were synthesized on Wang-resin using previously established Fmoc-SPPS protocols both manually and by a CS336X peptide synthesizer (CS Bio). Briefly, couplings were performed (twice or 3 times) using standard Fmoc-protected amino acids (3-fold molar excess) and as coupling reagents N,N,N',N'-tetramethyl-O-(1H-benzotriazol-1-yl)uronium hexafluorophosphate (HBTU) or 2-(7-aza-1H-benzotriazole-1-yl)-1,1,3,3-tetramethyluronium hexafluorophosphate (HATU) (3-fold molar excess) for selected couplings, and N,N-diisopropylethylamine (DIEA) (4.5 molar excess) in N,N-dimethylformamide (DMF). In the case of LL-37(1-14), most couplings were performed twice using HBTU as coupling agent except for Lys10, Glu11, and Lys12 for which HATU was used for the first coupling; in addition, 3 couplings were performed for Phe5, Phe6, and Arg7 using HATU for the first two of them. In the case of LL-37(15-37), most couplings were repeated three times using HATU for the first one and HBTU for the following ones; double couplings were performed only within LL-37(15-19), and for residues Lys25, Asp26, Pro33, and Arg34. Cleavages of the two LL-37 segments from the resin were carried out by trifluoroacetic acid/water (95/5, v/v) (3 h). Their RP-HPLC purifications were performed using a Nucleosil 100 C18 (250 mm×8 mm; particle size, 7 μm) column as described. Peptide purity (including the purity of commercially obtained LL-37, scrLL-37 and FAM-LL-37) was verified by MALDI-TOF MS. In the case of LL-37(1-14): found MH+, 1638.3 (calculated, 1638.9); in the case of LL-37(15-37), found MH+, 2873.9 (calculated, 2873.6). Stocks of LL-37 (1-14) and LL-37(15-37) were made in HFIP (4° C.) and their concentrations were determined by their weight and confirmed by the BCA assay.

Thioflavin T (ThT) Binding Assays

The effects of LL-37 and the other peptides on kinetics of IAPP fibrillogenesis were investigated by using the thioflavin T (ThT) binding assay using a previously established protocol. Briefly, IAPP alone (16.5 μM) and its mixtures with LL-37 and the other peptides were incubated in ThT assay buffer (aqueous 50 mM sodium phosphate buffer, pH 7.4, containing 100 mM NaCl and 0.5% HFIP) at the indicated molar ratios (20° C.) (non-stirring conditions). Of note, an incubation of LL-37 alone was also included. At the indicated time points aliquots were mixed with the ThT solution consisting of 20 μM ThT in 0.05 M glycine/NaOH (pH 8.5) and binding was determined by measuring fluorescence emission at 486 nm upon excitation at 450 nm using a Multilabel reader VictorX3 (Perkin Elmer Life Sciences). For studying the effect of LL-37 on nucleation of IAPP fibrillogenesis, i.e. following seeding with preformed IAPP fibrils (fIAPP) (10%), incubations of IAPP (16.5 μM) and its mixtures with LL-37 (1/1) were performed as above at room temperature. An aliquot of a solution consisting mostly of IAPP fibrils (fIAPP) based on ThT binding and TEM (FIGS. 18-19) (7 days aged IAPP (16.5 μM) made as above) was added to the incubations resulting in a final seed (fIAPP) concentration of 1.65 μM. Incubations of (unseeded) IAPP alone (16.5 μM) and of 10% fIAPP alone were included as controls. ThT binding was determined at the indicated time points as above. To study the effect of LL-37-treated IAPP fibrils (LL-37-treated fIAPP) on kinetics of IAPP fibrillogenesis in comparison to the seeding effect of fIAPP, an aliquot of a solution consisting mostly of fIAPP (16.5 μM fIAPP, 7 days aged; see above) was added to solid LL-37 (10-fold molar excess) and the mixture was incubated for 24 h yielding "LL-37-treated fIAPP" (FIG. 3*b*). Of note, binding of LL-37 to fIAPP was confirmed by a dot blot (DB) assay (FIG. 2*b* and data not shown); in addition, a DB assay was also applied to confirm that the same amounts of fIAPP were present in the aliquots of fIAPP and the LL-37-treated fIAPP used for the seeding assays (data not shown). An aliquot of the fIAPP containing solution (treated in the same way as the LL-37-treated aliquot but w/o LL-37) was used to determine the seeding effect of fIAPP. Solutions containing (unseeded) IAPP alone (16.5 μM), IAPP seeded with fIAPP (10%), and IAPP seeded with LL-37-treated fIAPP (10%) were made in ThT assay buffer and kinetics of fibrillogenesis were determined by the ThT binding assay as described above.

Assessment of Cell Damage by the MTT Reduction Assay

Effects of LL-37 and the other peptides on formation of β-cell damaging IAPP assemblies were studied in the rat insulinoma cell line RIN5fm using the peptide solutions applied for the ThT binding assays as previously described. Briefly, RIN5fm cells were cultured and plated in 96-well plates as described. Solutions of IAPP alone and its mixtures with peptides were aged in ThT assay buffer as described under "ThT binding assays". At the indicated incubation time points (24 h or 7 days) aliquots were diluted with cell culture medium and added to the cells. Following incubation with the cells for ~20 h (37° C., humified atmosphere containing 5% CO2), cell damage was verified by the MTT reduction assay. For the determination of the IC50 of the inhibitory effect of LL-37 on formation of cytotoxic IAPP aggregates, 24 h aged IAPP (100 nM) alone and its mixtures with various amounts of LL-37 (made as under ThT binding assay) were added to the cells and cell viability was determined by the MTT reduction assay as above.

Transmission Electron Microscopy (TEM)

TEM samples were prepared applying 10 μl aliquots of the solutions used in the ThT binding and MTT assays on carbon-coated grids at the indicated time points. The grids were washed using ddH2O and stained with aqueous 2% (w/v) uranyl acetate solution. Examination of the grids was done with a JEOL 1400 Plus electron microscope at 120 kV.

Far-UV CD Spectroscopy

Far-UV CD studies were performed using a Jasco 715 spectropolarimeter. Spectra were recorded at room temperature between 195 and 250 nm, at 0.1 nm intervals, and with a response time of 1 second. Each spectrum is an average of 3 spectra. All CD studies were performed in aqueous 10 mM sodium phosphate buffer (pH 7.4) containing 1% HFIP (CD assay buffer) at room temperature; this assay system has been earlier developed and found to be suitable for following kinetics of IAPP (5 μM) misfolding into β-sheets and amyloid fibrils alone or in the presence of inhibitors. Briefly, peptide stocks in HFIP were freshly made (4° C.), diluted with assay buffer (room temperature) at the indicated concentrations within the cuvette, and following gentle mixing spectra were measured immediately or at the indicated incubation time points. For the studies addressing the interactions between LL-37 or scrLL-37 and IAPP, peptide mixtures (1/1) were prepared in HFIP (4° C.) and diluted with assay buffer in the cuvette at the indicated concentrations (5 μM each) (room temperature); CD spectra were measured as above. Of note, CD studies on IAPP alone and LL-37 or scrLL-37 alone (from the same stocks; 5 μM) were also performed in parallel. The CD spectrum of IAPP at the incubation time point of 24 h (endpoint) was measured after gentle mixing to re-dissolve precipitated aggregates. The CD spectrum of the buffer was always subtracted from the CD spectra of the peptide solutions.

Fluorescence Spectroscopic Titrations

Fluorescence spectroscopic titration studies were performed with a JASCO FP-6500 fluorescence spectrophotometer using a previously described experimental protocol. Briefly, excitation was at 492 nm and emission spectra were recorded between 500 and 600 nm. The apparent (app.) Kds of the interactions of IAPP with LL-37 and its segments LL-37(1-14) and LL-37(15-37) were quantified by titrating synthetic Na-amino-terminal fluorescein labeled IAPP (5 nM) with various amounts of each of the peptides. For all experiments, freshly made stocks of peptides and their fluorescently labeled analogs in HFIP were used. Measurements were performed in 10 mM sodium phosphate buffer (pH 7.4) containing 1% HFIP within 2-5 min following solution preparation at room temperature. Of note, under these conditions freshly made Fluos-IAPP (5 nM) solutions consist mostly of monomers. App. Kds were calculated using 1/1 binding models as previously described and are means (±SD) of three binding curves.

Cross-Linking, NuPAGE, and Western Blot Analysis

Cross-linking studies were preformed using a previously developed assay system. Briefly, solutions of IAPP alone (30 μM) and its mixtures with LL-37 or scrLL-37 at the indicated molar ratios (IAPP/LL-37 at 1/1 or 1/0.1) were prepared in aqueous sodium phosphate buffer, pH 7.4, and incubated for 30 min at room temperature; of note, incubations of LL-37 alone (at the same concentrations as in its mixtures with IAPP) were made as well. Solutions were cross-linked using 25% aqueous glutaraldehyde (Sigma-Aldrich) and 10% aqueous trichloroacetic acid (TCA) was used to precipitate cross-linked peptides. Pellets were dissolved in reducing NuPAGE sample buffer, boiled for 5 min, and subjected to NuPAGE electrophoresis in 4-12% Bis-Tris gels with MES running buffer (Invitrogen). The same volume of each solution (same IAPP amount) was loaded in all lanes. Peptides were blotted using a XCell II Blot Module blotting system (Invitrogen). IAPP or LL-37 were detected using a polyclonal rabbit anti-IAPP antibody (Peninsula) or a monoclonal mouse anti-LL-37 antibody (Santa Cruz Biotechnology), respectively in combination with suitable peroxidase (POD)-coupled secondary antibodies (Pierce & Amersham) and the Super Signal West Dura Extended Duration Substrate (Pierce). Of note, previous studies provided evidence for the specificity of the cross-linking assay; in addition, no new bands were observed in IAPP-scrLL-37 (1/1) mixtures (data not shown).

Dot Blot Analysis

IAPP monomers or IAPP fibrils (fIAPP) containing solutions (different amounts up to 40 μg) were spotted onto a nitrocellulose membrane. These solutions were prepared by incubating an IAPP solution (1 mg/ml) in ThT assay buffer for 0 h ("monomers") or 24 h ("fibrils"); the presence of fibrils was confirmed by ThT binding and TEM (not shown). The membrane was washed with TBSn (20 mM Tris/HCl, 150 mM NaCl and 0.05% Tween-20), blocked with 5% milk in TBSn overnight at 10° C., and washed again with TBSn. Then, the membrane was incubated with N-terminal fluorescein labeled LL-37 (FAM-LL-37 from AnaSpec; see under "Peptides and peptide synthesis") (200 nM) in ThT assay buffer containing 1% HFIP overnight at 10° C. Following washings with incubation buffer and TBSn, bound FAM-LL-37 was visualized with a LAS-4000mini instrument (Fujifilm). Of note, glucagon fibrils were spotted as well to control for the specificity of the observed strong binding of FAM-LL-37 to fIAPP (not shown). Glucagon fibrils were made by incubating glucagon in 10 mM HCl (2 μg/μl) (10 days) followed by neutralization with 10 mM NaOH; ThT binding and TEM confirmed fibril formation (not shown). The ThT buffer alone was also spotted to control for NSB. In addition, to control for the interference of fibril autofluorescence, a membrane containing spotted fIAPP which had been incubated in buffer alone w/o FAM-LL-37 was included in each assay; in general, fIAPP autofluorescence contributed up to 25% of the total amount of fluorescence observed in fIAPP bound to FAM-LL-37.

Determination of LL-37 Binding Sites by Using Peptide Arrays

A peptide array consisting of LL-37 decamers covering the full length LL-37 sequence and positionally shifted by one residue was synthesized on a modified cellulose membrane support using stepwise SPOT synthesis protocols and a MultiPep RSi (Intavis) peptide synthesizer. Thereafter, peptides were immobilized on a glass slide according to the manufacturer's instructions followed by a blocking step using 1% BSA in TBSn for 4 h (room temperature). The glass slide with the peptide array was incubated with a solution of Fluos-IAPP (1 μM in TBSn containing 1% BSA) for ~12 h at 10° C. followed by washing with TBSn. Visualization of bound Fluos-IAPP was performed with a LAS-4000mini instrument (Fujifilm).

Sequence Alignment Using LALIGN

The sequence alignment of IAPP and LL-37 was done with the program LALIGN (Author: Bill Pearson; https://embnet.vital-it.ch/software/LALIGN_form.html). Of note, this program was previously used for the comparison of the Aβ and IAPP sequences to each other. A global alignment method was used with 3 reported sub-alignments; E-value threshold was set to 10.0, the scoring matrix used is BLOSUM50, opening gap penalty was set to −12 and extending gap penalty to −2 (default values). The LALIGN program implements the algorithm of Huang and Miller.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A method for treating type 2 diabetes (T2D), comprising:
   - diagnosing a subject as suffering from T2D or as being pre-diabetic;
   - monitoring the response to glucose stimulation of at least one islet in the pancreas of the subject by quantitatively imaging glucose metabolism in vivo;
   - establishing a target range for the response to glucose stimulation of the at least one islet; and
   - upregulating cathelicidin gene expression in the subject until the monitored response to glucose stimulation is within the target range.

2. The method of claim 1, wherein monitoring the response to glucose stimulation includes determining the response to glucose stimulation of the at least one islet occurs in real time.

3. The method of claim 1, wherein monitoring the response to glucose stimulation includes quantitatively imaging real-time glucose metabolism from single islets in vivo.

4. The method of claim 1, wherein monitoring the response to glucose stimulation includes utilizing intrinsic autofluorescence in combination with multiphoton excitation microscopy.

5. The method of claim 1, wherein monitoring the response to glucose stimulation includes quantitatively imaging glucose metabolism in vivo to repeatedly measure the response of the at least one islet to glucose stimulation.

6. The method of claim 1, wherein monitoring the response to glucose stimulation further includes monitoring at least one parameter selected from the group consisting of islet function, proliferation, vasculature and macrophage infiltration.

7. The method of claim 1, wherein quantitatively imaging glucose metabolism includes NAD(P)H imaging.

8. The method of claim 7, wherein monitoring the response to glucose stimulation includes:
   - directly measuring glucose metabolism; and
   - correlating autofluorescence signals with downstream glucose-stimulated events.

9. The method of claim 7, wherein the NAD(P)H imaging uses an interdependence between NAD(P)H and intracellular $Ca^{2+}$ to measure pancreatic β-cell function.

10. The method of claim 7, further comprising:
   - monitoring redox state and mitochondrial function by quantifying cellular NAD(P)H.

11. The method of claim 7, further comprising:
   - measuring cytoplasmic and mitochondrial NAD(P)H changes to resolve the spatiotemporal partitioning of glycolytic and oxidative metabolism.

12. The method of claim 1, wherein quantitatively imaging glucose metabolism in vivo includes the use of a β-Amyloid imaging probe.

13. The method of claim 12, wherein the β-Amyloid imaging probe is selected from the group consisting of IPBF, PQ-6, FPYBF-1, IMPY and AV-45 imaging probes.

14. The method of claim 13, wherein the β-Amyloid imaging probe is [$^{125}$I]IPBF.

15. The method of claim 1, wherein monitoring the response to glucose stimulation of at least one islet includes the use of positron emission tomography (PET) in combination with an amyloid imaging probe.

16. The method of claim 15, wherein the amyloid imaging probe is a $^{18}$F-labelled radiopharmaceutical.

17. The method of claim 1, wherein diagnosing a subject as being pre-diabetic includes administering to the subject a test selected from the group consisting of the Fasting Plasma Glucose (FPG) test, the Oral Glucose Tolerance Test (OGTT), and the Random Plasma Glucose test.

18. The method of claim 1, wherein upregulating cathelicidin gene expression in the subject includes administering to the subject a pharmaceutically acceptable composition which upregulates cathelicidin gene expression and wherein said mixture includes at least three materials selected from the group consisting of phenylbutyrate, bexarotene, curcumin, resveratrol, retinol, betacarotene, cholecalciferol, and pharmaceutically acceptable salts thereof.

19. A method for treating a subject, comprising:
   - monitoring levels of the cathelicidin peptide LL-37 in the blood of a subject and IAPP amyloid in pancreatic tissues of the subject; and
   - when the condition $L/B<k$ is detected, where L is the level of LL-37 detected, B is the level of IAPP detected, and k is a predetermined threshold value, upregulating cathelicidin gene expression in the subject.

20. A method for treating a subject for type 2 diabetes (T2D), comprising:

diagnosing the subject as suffering from T2D; and applying to the subject a pharmaceutically acceptable composition comprising a peptidomimetic of LL-37 or a portion thereof.

* * * * *